(12) United States Patent
Dutreix et al.

(10) Patent No.: US 6,936,418 B2
(45) Date of Patent: Aug. 30, 2005

(54) METHODS AND COMPOSITIONS FOR EFFECTING HOMOLOGOUS RECOMBINATION

(75) Inventors: Marie Dutreix, L'Hay les Roses (FR); Jian-Sheng Sun, Aulnay Sous Bois (FR); Elodie Biet, Paris (FR); Rosalie Maurisse, Paris (FR); Jean-Paul Feugeas, Brunoy (FR)

(73) Assignees: Institut Curie, Paris (FR); Centre National de la Recherche Scientifique, Paris (FR); Museum National D'Histoire Naturelle, Paris (FR); Institut National de la Sante et de la Recherche Medicale, Paris (FR)

( * ) Notice: Subject to any disclaimer, the term of this patent is extended or adjusted under 35 U.S.C. 154(b) by 0 days.

(21) Appl. No.: 10/053,526

(22) Filed: Jan. 18, 2002

(65) Prior Publication Data

US 2003/0003547 A1 Jan. 2, 2003

Related U.S. Application Data

(63) Continuation of application No. PCT/IB01/00749, filed on May 3, 2001.

(30) Foreign Application Priority Data

May 3, 2000 (EP) ............................................. 00401218

(51) Int. Cl.[7] .......................... C12Q 1/68; C12N 15/87; C07H 21/02
(52) U.S. Cl. ........................... 435/6; 435/440; 435/462; 435/463; 435/91.2; 536/23.1
(58) Field of Search ................................. 435/463, 462, 435/440, 6, 91.2; 536/23.1

(56) References Cited

U.S. PATENT DOCUMENTS 5,770,408 A * 6/1998 Sato ........................... 435/91.2
5,876,976 A * 3/1999 Richards et al. ............ 435/91.2

FOREIGN PATENT DOCUMENTS

| WO | 96/40271 | 12/1996 | .......... A61K/48/00 |
| WO | 96/40711 | 12/1996 | ........... C07H/21/00 |
| WO | 96/41008 | 12/1996 | ............ C12Q/1/68 |
| WO | 00/09755 | 2/2000 | ............ C12Q/1/68 |

OTHER PUBLICATIONS

Erdeniz et al, "Cloning–free PCR based allele replacement methods", Genome Research 7:1174–1183.*
Puri et al, "Targeted gene knockout by 2'-O-aminoethyl modified triplex forming oligonucleotides", J. Blol. Chem. (2001) 276(31):28991–28998.*
Lin et al, "Stability of DNA triplexes on shuttle vector plasmids in the replication pool in Mammalian cells", J. Biol. Chem. (2000) 275(50):39117–39124.*
Uhlman et al, "antisense oligonucleotides: A new therapeutic principle", Chemical Reviews 90(4):543–584), Jun. 1990.*
Rubnitz et al (Mol. Cell. Biol. (1984) 4:2253–2258).*
Thibaut Michel, et al., "Cationic phosphoramidate α–oligonucleotides efficiently target single–stranded DNA and RNA and inhibit hepatitis C virus IRES–mediated translation", Nucleic Acids Research, vol. 3, No. 18, Jul. 2003, ppp. 5282–5290.
Vasquez, Karen M., et al., "Specific Mutations Induced by Triplex–Forming Oligonucleotides in Mice", Science, vol. 290, Oct. 2000, pp. 530–533.
Vasquez, Karen M., et al., "Chromosome Targeting at Short Polypurine Sites by Cationic Triplex–forming Oligonucleotides," The Journal of Biological Chemistry, vol. 276, No. 42, Oct. 2001, pp. 38536–38541.
Bailey, Cheryl P., et al., "Cationic oligonucleotides can mediate specific inhibition of gene expression in Xenopus oocytes," Nucleic Acids Research, vol. 26, No. 21, 1998, pp. 4860–4867.
Dagle, John M., "Positively charged oligonucleotides overcome potassium–medited inhibition of triplex DNA formation," Nucleic Acids Research, Vo. 24, No. 11, 1996, pp. 2143–2149.
Hillbrand, Stefan, et al, "5–Substituted 2–Aminopyridine C–Nucleosides as Protonated Cytidine Equivalents: Increasing Efficiency and Selectivity in DNA Triple–Helix Formation," J. Am. Chem. Soc., 119, 1997, pp. 5499–5511.
Cassidy, Sarah A., et al., "Recognition of GC base pairs by triplex forming oligonucleotides containing nucleosides derived from 2–aminopyridine," Nucleic Acids Research, vol. 25, No. 24, 1997, pp. 4891–4898.
Wang et al., "Peptide nucleic acid (PNA) binding—mediated gene regulation", Cell Research, vol. 14, No. 2, pp. 111–116 (2004).
Biet Elodie et al., "Stimulation of RecA–mediated D–loop formation by oligonucleotide–directed triple–helix formation: Guided homologous recombination (GOREC)" Biochemistry, vol. 40, No. 6, Feb. 13, 2001 pp 1779–1786.
H.B. Gamper et al., "Strand invasion of supercoiled DNA by oligonucleotides with a triplex guided sequence", J. Am. Chem. Society, vol. 120, 1998, pp. 2182–2183.
Culver Kenneth W. et al., "Correction of chromosomal point mutations in human cells with bifunctional oligonucleotides" Nature Biotechnology, vol. 17, No. 12, Oct. 1999, pp. 989–993.

(Continued)

*Primary Examiner*—Jeffrey Fredman
(74) *Attorney, Agent, or Firm*—Darby & Darby

(57) ABSTRACT

This invention concerns a method for effecting directed mutagenesis based on a guided homologous recombination system that comprises (i) a triple helix forming oligonucleotide, (ii) a donor nucleic acid segment, and (iii) an adapter segment comprising an oligonucleotide sequence able to bind at least a portion of said donor nucleic acid through Watson-Crick base pairing.

2 Claims, 11 Drawing Sheets

OTHER PUBLICATIONS

Chan Phillip P. et al., "Targeted correction of an episomal gene in mammalian cells by a short DNA fragment tethered to a triplex–forming oligonucleotide" Journal of Biological Chemistry, vol. 274, No. 17, Apr. 23, 1999, pp. 11541–11548.

Cole–Strauss Allyson et al., "Targeted gene repair directed by the chimeric RNA/DNA oligonucleotide in a mammalian cell–free extract", Nucleic Acids Research, vol. 27, No. 5, Mar. 1, 1999, pp. 1323–1330.

Escude Christophe et al., "Padlock oligonucleotides for duplex DNA based on sequence–specific teiple helix formation" Proceedings of the National Academy of Sciences of the United States, vol. 96, No. 19, pp. 10603–10607.

* cited by examiner

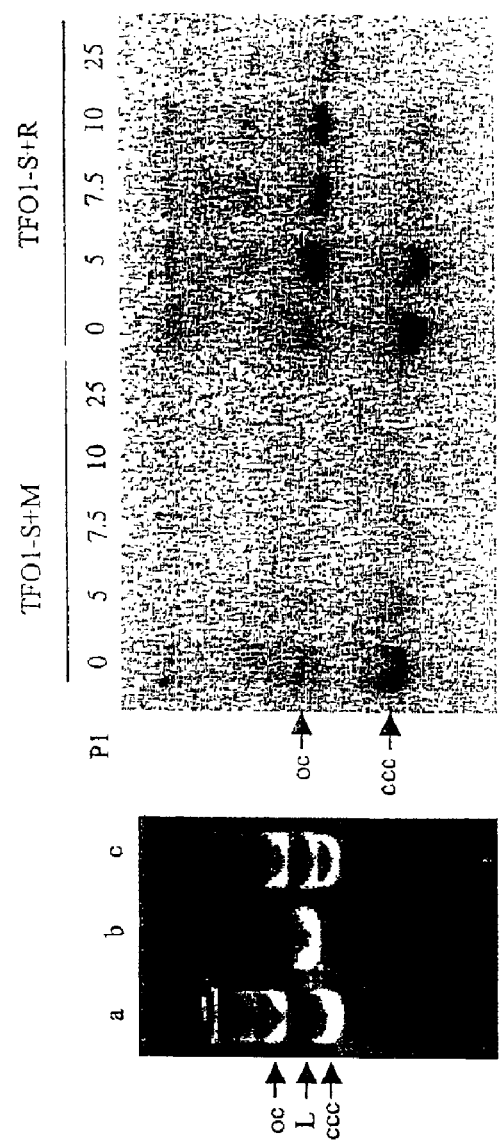

SEQUENCE LISTING

```
<160> NUMBER OF SEQ ID NOS: 19

<210> SEQ ID NO 1
<211> LENGTH: 28
<212> TYPE: DNA
<213> ORGANISM: artificial
<220> FEATURE:
<223> OTHER INFORMATION: oligonucleotide

<400> SEQUENCE: 1
cgtctagaaa agaaaagggg ggatacgc                                       28

<210> SEQ ID NO 2
<211> LENGTH: 28
<212> TYPE: DNA
<213> ORGANISM: artificial
<220> FEATURE:
<223> OTHER INFORMATION: oligonucleotide

<400> SEQUENCE: 2
gcgtatcccc ccttttcttt tctagacg                                       28

<210> SEQ ID NO 3
<211> LENGTH: 12
<212> TYPE: DNA
```

-continued

```
<213> ORGANISM: artificial
<220> FEATURE:
<223> OTHER INFORMATION: oligonucleotide

<400> SEQUENCE: 3
gccgtggcca gc                                                              12

<210> SEQ ID NO 4
<211> LENGTH: 11
<212> TYPE: DNA
<213> ORGANISM: artificial
<220> FEATURE:
<223> OTHER INFORMATION: oligonucleotide

<400> SEQUENCE: 4
gctggccagc g                                                               11

<210> SEQ ID NO 5
<211> LENGTH: 40
<212> TYPE: DNA
<213> ORGANISM: artificial
<220> FEATURE:
<223> OTHER INFORMATION: oligonucleotide

<400> SEQUENCE: 5
ccgggtctag aaaagaaaag gggggatacg cgtggccagc                                 40

<210> SEQ ID NO 6
<211> LENGTH: 40
<212> TYPE: DNA
<213> ORGANISM: artificial
<220> FEATURE:
<223> OTHER INFORMATION: oligonucleotide

<400> SEQUENCE: 6
ccggcgtggc cacgcgtatc cccccttttc ttttctagac                                 40

<210> SEQ ID NO 7
<211> LENGTH: 21
<212> TYPE: DNA
<213> ORGANISM: artificial
<220> FEATURE:
<223> OTHER INFORMATION: oligonucleotide

<400> SEQUENCE: 7
ccggtcgcca ccatggtgag c                                                    21

<210> SEQ ID NO 8
<211> LENGTH: 20
<212> TYPE: DNA
<213> ORGANISM: artificial
<220> FEATURE:
<223> OTHER INFORMATION: oligonucleotide

<400> SEQUENCE: 8
cgcgtggcca gctcgagatc                                                      20

<210> SEQ ID NO 9
<211> LENGTH: 12
<212> TYPE: DNA
<213> ORGANISM: artificial
<220> FEATURE:
<223> OTHER INFORMATION: oligonucleotide

<400> SEQUENCE: 9
cgcgtggcca gc                                                              12
```

<210> SEQ ID NO 10
<211> LENGTH: 17
<212> TYPE: DNA
<213> ORGANISM: artificial
<220> FEATURE:
<223> OTHER INFORMATION: oligonucleotide
<220> FEATURE:
<221> NAME/KEY: misc_feature
<222> LOCATION: (1)..(17)
<223> OTHER INFORMATION: n is a or g or c or t/u, unknown, or other

<400> SEQUENCE: 10
nnnnntntnn ngnggng                                               17

<210> SEQ ID NO 11
<211> LENGTH: 17
<212> TYPE: DNA
<213> ORGANISM: artificial
<220> FEATURE:
<223> OTHER INFORMATION: oligonucleotide
<220> FEATURE:
<221> NAME/KEY: misc_feature
<222> LOCATION: (1)..(17)
<223> OTHER INFORMATION: n is a or g or c or t/u, unknown, or other

<400> SEQUENCE: 11
nnntntntnt ngggggg                                               17

<210> SEQ ID NO 12
<211> LENGTH: 65
<212> TYPE: DNA
<213> ORGANISM: artificial
<220> FEATURE:
<223> OTHER INFORMATION: oligonucleotide

<400> SEQUENCE: 12
cgtctagaaa agaaaagggg ggatacgcgt ggccagctac atataagtaa cgtgctgcta       60
ctcat                                                                  65

<210> SEQ ID NO 13
<211> LENGTH: 65
<212> TYPE: DNA
<213> ORGANISM: artificial
<220> FEATURE:
<223> OTHER INFORMATION: oligonucleotide

<400> SEQUENCE: 13
gcagatcttt tcttttcccc cctatgcgca ccggtcgatg tatattcatt gcacgacgat       60
gagta                                                                  65

<210> SEQ ID NO 14
<211> LENGTH: 18
<212> TYPE: DNA
<213> ORGANISM: artificial
<220> FEATURE:
<223> OTHER INFORMATION: oligonucleotide

<400> SEQUENCE: 14
tcttttcttt tcccccct                                              18

<210> SEQ ID NO 15
<211> LENGTH: 12
<212> TYPE: DNA
<213> ORGANISM: artificial
<220> FEATURE:

```
<223> OTHER INFORMATION: oligonucleotide

<400> SEQUENCE: 15
cgcgtggcca gc                                                          12

<210> SEQ ID NO 16
<211> LENGTH: 40
<212> TYPE: DNA
<213> ORGANISM: artificial
<220> FEATURE:
<223> OTHER INFORMATION: oligonucleotide

<400> SEQUENCE: 16
gcgcaccggt cgatgtatat tcattgcacg acgatgagta                            40

<210> SEQ ID NO 17
<211> LENGTH: 40
<212> TYPE: DNA
<213> ORGANISM: artificial
<220> FEATURE:
<223> OTHER INFORMATION: oligonucleotide

<400> SEQUENCE: 17
gcgcaccggt cgaagaaaaa tgcatggacc accatcagaa                            40

<210> SEQ ID NO 18
<211> LENGTH: 37
<212> TYPE: DNA
<213> ORGANISM: artificial
<220> FEATURE:
<223> OTHER INFORMATION: oligonucleotide

<400> SEQUENCE: 18
gctggccacg cgtatccccc cttttctttt ctagacg                               37

<210> SEQ ID NO 19
<211> LENGTH: 37
<212> TYPE: DNA
<213> ORGANISM: artificial
<220> FEATURE:
<223> OTHER INFORMATION: oligonucleotide

<400> SEQUENCE: 19
cgaccggtgc gcataggggg gaaaagaaaa gatctgc                               37
```

METHODS AND COMPOSITIONS FOR EFFECTING HOMOLOGOUS RECOMBINATION

This is a continuation of international application Ser. No. PCT/IB01/00749, filed May 3, 2001, the entire disclosure of which is hereby incorporated by reference.

The invention relates to a method of directed mutagenesis based on both oligonucleotide-directed triple helix formation and homologous recombination.

In particular, the invention provides a method for effecting gene alteration or mutation repair at a specific-sequence site on a native DNA.

BACKGROUND

Since the end of 1987, oligonucleotide-directed triple helix formation (Le Doan et al, 1987; Moser et al, 1987) has risen considerable interests because it provides an elegant rational basis for gene-specific DNA targeting, therefore for interfering with gene expression at transcriptional level and other biological process (Hélène et al, 1991; Chan et al, 1997). In the last decade, intense research in this field has paved physico-chemical and biochemical basis for developing high affinity and nuclease-resistant triple helix-forming oligonucleotides (TFOs) (Thuong et al, 1993; Sun et al, 1996). It has been shown that transcription can be effectively inhibited by forming stable triple helix that competes either with the binding of transcriptional factors at gene regulation region (promoter/enhancer) or with the elongation of RNA polymerase (Guieysse et al, 1996; Giovannangeli et al, 1996). Furthermore, it has been demonstrated that, at least, some of the target DNA sequences in chromatin environment are accessible to TFOs (Gionvannangeli et al, 1997; Belousov et al, 1998).

In parallel with the development of the so-called "antigene strategy", sequence-specific targeting of Watson-Crick double-stranded DNA (dsDNA) has been exploited to create diverse new tools for molecular and cellular biology (Maher et al, 1996; Thuong et al, 1993). TFOs have been successfully converted to artificial nucleases by covalent attachment of a DNA cleaving reagent (including metal chelating complexes, alkylating or photoactivating agents and nucleases) (Moser et al, 1987; Francois et al, 1989; Pei et al, 1991) or by combination of a couple of methylase/restriction enzyme (known as Achilles Heel approach) (Strobel et al, 1991) or most recently by recruiting topoisomerase (Matteucci et al, 1997; Arimondo et al, 1999). It has also been used to bend DNA (Akiyama et al, 1996) and to padlock dsDNA (Escudé et al, 1999).

Inter-strand cross-linked DNA by TFO-psoralen conjugates has been shown to trigger DNA repair events that lead to site-specific mutagenesis (Havre et al, 1993; Barre et al, 1999). Such an application of TFOs is potentially useful because many known disease and pathologies originate from mutation in DNA sequences. In general, the correct repair of mutant gene either by directed mutagenesis or by homologous recombination might help to cure these diseases. However, the lack of efficient tools for directed mutagenesis in mammal cells has so far hampered significant progress in this field in part due to very low frequency of homologous recombination (10-8-10-5) (Bollag et al, 1989) and high background of random integration of transfected DNA (Roth et al, 1986).

Recent progress has been made in targeted gene repair directed by the chimeric RNA/DNA oligonucleotides in mammalian cells (Yoon et al, 1996; Alexeev et al, 1998 and Cole-Strauss et al, 1999).

The current development of triplex-directed mutagenesis and recombination benefits from the sequence-specific recognition of dsDNA by TFO and the efficient DNA inter-strand cross-linking by a mutagen, namely psoralen which is covalently attached to a TFO.

WO 96/41 008 discloses a method for effecting homologous recombination between a native nucleic acid segment and a donor nucleic acid by formation of a triple helix between an oligonucleotide and one or two DNA strands in the vicinity of a target region wherein recombination is to occur, the oligonucleotide being capable of triggering an homologous recombination in the target region with the donor nucleic acid segment.

The triple helix-forming oligonucleotide is chemically modified to include a mutagen at either the 5' end, 3' end, or internal portion so that the mutagen is proximal to a site where it will cause modification or damage to the nucleic acid.

However, mutational event generated by error-prone repair of such a mutagen-TFO conjugate generally produces an unpredictable and a widespread spectrum of mutations and deletions. Therefore, its potential use as a therapeutic agent is compromised, especially when one think about the well known genotoxic and mutagenic effect of mutagenesis themselves.

Chan et al (1999) disclose a method of homologous recombination based on oligonucleotid-directed triple helix formation, wherein the TFO segment is covalently attached via a flexible linker to the donor segment.

Culver et al (1999) disclose a sequence-specific genomic targeting system for the correction of chromosomal mutations comprising two different binding domains incorporated into a single-stranded nucleotide. Namely, the targeting system comprises a first domain capable of forming a triplex by means of Hoogsteen interactions and a second domain capable of forming a heteroduplex which is covalently attached to the first domain by means of a linker segment.

However, there was a need for a new method of directed mutagenesis based on oligonucleotide-directed triple helix formation and homologous recombination which has a high efficiency of recombination, is mutagen-free, and which allows mutagenesis at a site which is not distance-limited on the triple helix-forming site.

SUMMARY OF THE INVENTION

The present invention provides a method for effecting an homologous recombination between a double-stranded native nucleic acid segment in a cell and a donor nucleic acid segment introduced into the cell, which method comprises the steps consisting of:

a) introducing into a cell a nucleic acid targeting system comprising:

(i) a third strand oligonucleotide which comprises a base sequence capable of forming a triple helix at a binding region on one or both strands of a native nucleic acid segment, (ii) a donor nucleic acid, comprising a nucleic acid sequence substantially homologous to the native nucleic acid segment so that the donor sequence is capable of undergoing homologous recombination with the native sequence at the target region, (iii) an adapter segment comprising an oligonucleotide sequence able to bind at least a portion of said donor nucleic acid through Watson-Crick base pairing, the adapter segment being linked to said third strand oligonucleotide, b) allowing the third strand oligonucleotide to bind to the native nucleic acid segment to form a triple helix nucleic acid, thereby inducing homologous recombination at the native nucleic acid segment target region; and c) allowing homologous recombination to occur between the native and donor nucleic acid segments.

In the above method, said donor nucleic acid may be prepared by chemical synthesis of by an amplification method. Preferably, the donor nucleic acid may be selected from the group consisting of a double-stranded nucleic acid, a substantially complementary pair of single stranded nucleic acids and a single stranded nucleic acid When the donor nucleic acid is prepared by amplification before annealing to the adapter segment, the invention may comprise the steps consisting of:

a) providing a pair of primers complementary of the 5' and 3' ends of a double-stranded first native nucleic acid sequence;

b) amplifying said first native nucleic acid sequence, c) isolating the amplification product thus obtained;

d) annealing the amplification product with an adapter segment comprising an oligonucleotide sequence able to bind at least a portion of the nucleotide sequence of said amplified nucleic acid through Watson-Crick base pairing, said adapter segment being linked to a third strand oligonucleotide which comprises a base sequence capable of forming a triple helix at a binding region on one or both strands of a second native nucleic acid segment, thereby providing a nucleic acid targeting system comprising:

i) said third strand oligonucleotide, ii) said amplification product as a donor nucleic acid segment, and iii) said adapter segment bound to said donor nucleic acid segment through Watson-Crick base pairing;

e) introducing said nucleic acid targeting system into a cell comprising a second native nucleic acid different from the first native nucleic acid;

f) allowing the third strand oligonucleotide to bind to the second native nucleic acid segment to form a triple helix nucleic acid, thereby inducing homologous recombination at the second native nucleic acid segment target region; and g) allowing homologous recombination to occur between the second native and donor nucleic acid segments.

In another embodiment, the adapter segment itself can be used as a primer for the amplification of the donor nucleic acid. The method according to the invention may thus comprise the steps consisting of:

a) providing a pair of primers complementary to the 5' and 3' ends of a first double-stranded native nucleic acid sequence, wherein one of the primers is an adapter segment linked to a third strand oligonucleotide that comprises a base sequence capable of forming a triple helix at a binding region on one or both strands of a second double-stranded native nucleic acid segment;

b) amplifying said first native nucleic acid sequence, c) isolating the amplification product thus obtained, thereby providing a nucleic acid targeting system comprising:

i) said third strand oligonucleotide, ii) said amplification product as a donor nucleic acid segment, and iii) said adapter segment bound to a strand of said donor nucleic acid segment through Watson-Crick base pairing;

d) introducing said nucleic acid targeting system into a cell comprising a second native nucleic acid different from the first native nucleic acid;

e) allowing the nucleotide to bind to the second native nucleic acid segment to form a triple helix nucleic acid, thereby inducing homologous recombination at the second native nucleic acid segment target region; and f) allowing homologous recombination to occur between the second native and donor nucleic acid segments.

According to the above method, one amplified DNA strand is covalently linked to the adapter whereas the other one interacts with the adapter through Watson-Crick interactions. The latter strand can be considered as a single-stranded amplified donor nucleic acid. However, the above method can be modified so as to generate an amplified double-stranded donor nucleic acid that interacts with the adapter through Watson-Crick base pairing only. This can be readily achieved for example by introducing at least a ribonucleotide in the 3'-end of the adapter sequence and, further to the amplification step, applying a suitable treatment to destroy said ribonucleotide(s), such as enzymatic or mild alkaline treatment.

Accordingly the invention may provides a method for effecting an homologous recombination that comprises the steps consisting of:

a) providing a pair of primers complementary to the 5' and 3' ends of a first double-stranded native nucleic acid sequence, wherein one of the primers is a modified adapter segment which contains one or several ribonucleotide(s) at its 3'-end, wherein said adapter segment is linked to a third strand oligonucleotide which comprises a base sequence capable of forming a triple helix at a binding region on one or both strands of a second double-stranded native nucleic acid segment;

b) amplifying said first native nucleic acid sequence, c) isolating the amplification product thus obtained, d) treating the isolated amplification product in conditions sufficient to allow destruction of said ribonucleotide, thereby providing a nucleic acid targeting system comprising:

i) said third strand oligonucleotide, ii) said amplification product as a donor nucleic acid segment, and iii) said adapter segment bound to said donor nucleic acid segment through Watson-Crick base pairing;

e) introducing said nucleic acid targeting system into a cell comprising a second native nucleic acid different from the first native nucleic acid;

f) allowing the nucleotide to bind to the second native nucleic acid segment to form a triple helix nucleic acid, thereby inducing homologous recombination at the second native nucleic acid segment target region; and g) allowing homologous recombination to occur between the second native and donor nucleic acid segments.

In a preferred embodiment, said adapter is linked to said third strand oligonucleotide through a spacer.

The method according to the invention is particularly useful to replace a native nucleic acid that contains a mutation to be corrected by the homologous recombination.

The invention further relates to a kit that comprises:

i) a third strand oligonucleotide which comprises a base sequence capable of forming a triple helix at a binding region on one or both strands of a native nucleic acid segment;

ii) a donor nucleic acid, comprising a nucleic acid sequence substantially homologous to the native nucleic acid segment so that the donor sequence is capable of undergoing homologous recombination with the native sequence at the target region;

iii) an adapter segment comprising an oligonucleotide sequence able to bind at least a portion of said donor nucleic acid through Watson-Crick base pairing, the adapter segment being linked to said third strand oligonucleotide.

Finally, the invention provides a method for effecting gene alteration or mutation repair at a specific-sequence site on a native DNA, comprising:

a) introducing into a cell a nucleic acid targeting system comprising:

(i) a third strand oligonucleotide which comprises a base sequence capable of forming a triple helix at a binding region on one or both strands of a native nucleic acid segment, (ii) a donor nucleic acid, comprising a nucleic acid sequence substantially homologous to the native nucleic acid segment such that the donor sequence is capable of undergoing homologous recombination with the native sequence at the target region, (iii) an adapter segment comprising an oligonucleotide sequence able to bind at least a portion of said donor nucleic acid through Watson-Crick base pairing, the adapter segment being linked to said third strand oligonucleotide, b) allowing the oligonucleotide to bind to the native nucleic acid segment to form a triple helix nucleic acid, thereby inducing homologous recombination at the native nucleic acid segment target region; and c) allowing homologous recombination to occur between the native and donor nucleic acid segments, thereby performing that gene alteration or mutation repair.

BRIEF DESCRIPTION OF THE DRAWINGS

FIG. 3A: Gel retardation of different triplex systems in 10% non-denaturing polyacrylamide gel.

FIG. 6 represents the results of analysis of the enzyme digestion protection of Y0Gorec plasmid or recombinant ssDNA fragment by joint molecule formation. Panel A: Xba I restriction enzyme digestion. Joint molecules formed with TFO∅-S+R (lane b) or TFO1-S+R (lane c) were treated by Xba I enzyme. The undigested plasmid was run on the same gel (lane a). Panel B: Analysis of P1 nuclease digestion protection of the homologous R or heterologous M oligonucleotides in joint molecules. Joint molecules were formed by incubating DNAs with RecA protein for 45 minutes and treated with 0, 5, 7.5, 10 and 25 units×10$^{-4}$ of P1 enzyme (see below). oc: open circle; ccc: supercoiled plasmid. L:linear plasmid;

DETAILED DESCRIPTION OF THE INVENTION

Figure 1:
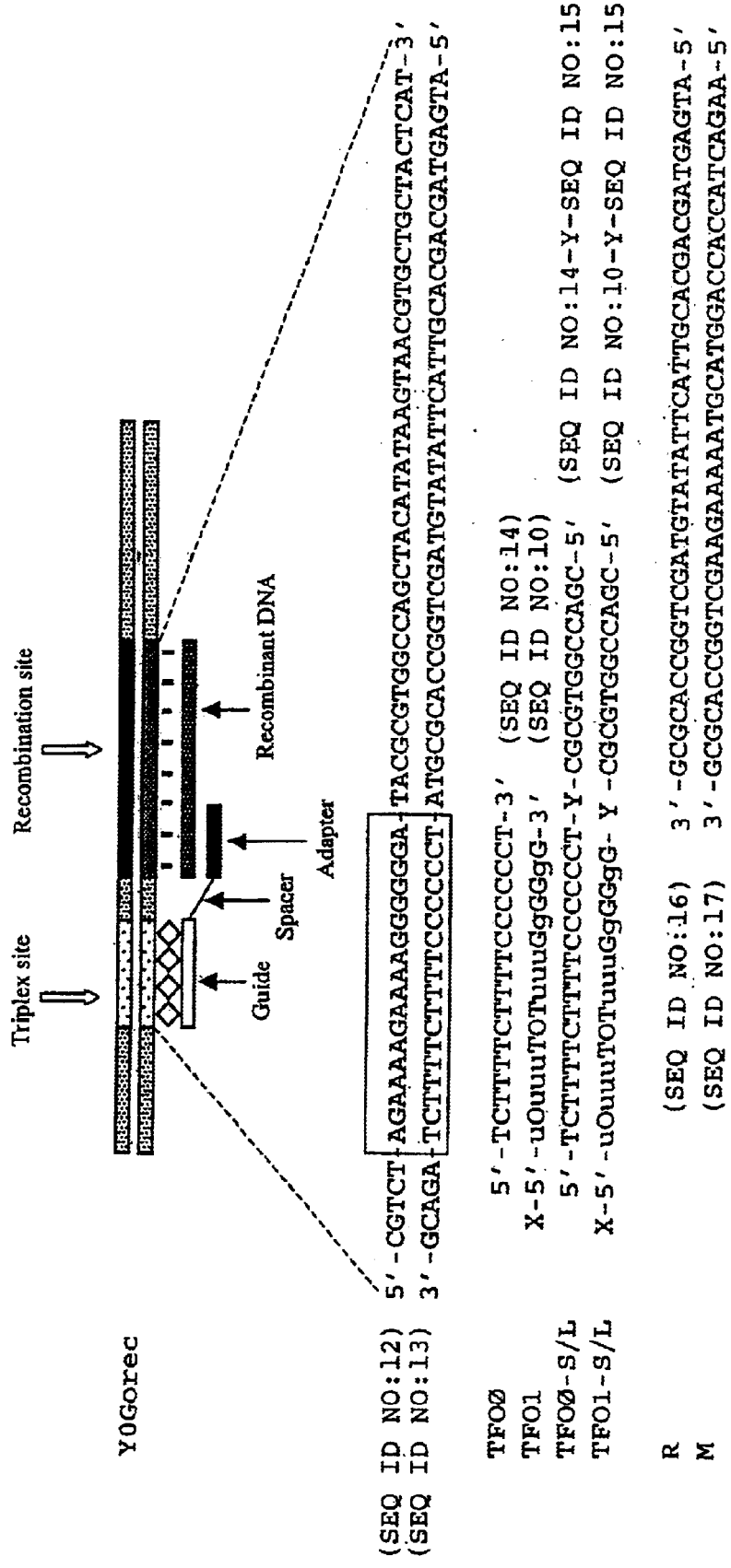
FIG. 1 is a schematic representation of Guided hOmologous RECombination (GOREC) systems of the invention and the sequences used as well as their notations (A). The 18-bp oligopyrimidine·oligopurine sequence for triplex formation is highlighted by a box. (contained within SEQ ID NOs 12 and 13). TFO1 is shown as SEQ ID NO: 10 and TFO∅ is shown as SEQ ID NO:14. The 12-nucleotide adapter is shown as SEQ ID NO:15. Hoogsteen hydrogen bonds between TFO and the target sequence are illustrated as diamonds and Watson-Crick interactions involved in D-loop between the recombinant fragment and the homologous duplex are indicated as vertical bars.

In prior art recombination systems, triple helix-forming oligonucleotides (TFOs) have been chosen to guide homologous donor DNA (DD) to its intended target site on genomic DNA and to position it for efficient information transfer via homologous recombination and/or gene conversion. In this approach, TFO is covalently tethered to DD through a linker. The effectiveness of the TFO-DD conjugate could be explained by: (i) an increase in the local concentration of DD; and (ii) a stimulation of DNA repair by triple helix formation that could provoke recruitment of proteins involved in homologous pairing, strand exchange and/or recombination.

The instant invention provides a new approach, named "GOREC" (for Guided hOmologous RECombination), which shares similar gene targeting strategy by oligonucleotide-directed triple helix formation, but has notable difference in the concept. It is made of a homing device (TFO) and a donor DNA (DD) for effecting distinct functions. They are joined together by non-covalent interaction through an adapter oligonucleotide, which is covalently linked to TFO. This modular concept allows to guide not only an oligonucleotide (natural and modified oligonucleotide (ODN), or RNA-DNA chimeric oligonucleotide (RDO)) but also a small DNA fragment (either single- or double-stranded) to the target site for homologous replacement. Therefore, the target site is not restricted to the vicinity of the triple helix site as is the case for the TFO-DD conjugate and can be hundreds base pairs away from the triplex site.

The inventors' in vitro study showed that the presence of TFO accelerates the D-loop formation between DD and the target DNA in the presence of RecA protein, and both triplex and D-loop are formed in the joint molecule (an obligatory intermediate and a limiting step in homologous recombination process). These data are consistent with the rational of GOREC approach in order to stimulate the early stages of homologous recombination by improving two limiting steps: (i) search of sequence homology; (ii) stability of recombinase-mediated transient complex, i.e. the joint molecule. The knowledge of the kinetic behavior, i.e. the lifetime, of triplex and the duplex formed by adapter and donor DNA allows fine-tuning of GOREC system.

The present invention therefore provides a nucleic acid targeting system that allows site-directed correction of genetic defects and gene alterations in cells.

As used herein, the term "oligonucleotide" refers to a nucleic acid, that is hybridizable to a genomic DNA molecule, a cDNA molecule, or a mRNA molecule encoding a gene, mRNA, cDNA, or other nucleic acid of interest. The nature of hybridization may involve Watson-Crick, reverse Watson-Crick, Hoogsteen or reverse Hoogsteen hydrogen bonding.

A nucleic acid molecule is "hybridizable" to another nucleic acid molecule, when a single stranded form of the nucleic acid molecule can anneal to the other nucleic acid molecule under the appropriate conditions of temperature and solution ionic strength (Sambrook et al., 1989). The conditions of temperature and ionic strength determine the "stringency" of the hybridization. "High stringency" refers to hybridization and/or washing conditions at 68° C. in 0.2×SSC, at 42° C. in 50% formamide, 4×SSC, or under conditions that afford levels of hybridization equivalent to those observed under either of these two conditions. SCC is a 0.15 M NaCl, 0.015 M Na-citrate. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. In a specific embodiment, the term "standard hybridization conditions" refers to a Tm of 55° C., and utilizes conditions as set forth above. In a preferred embodiment, the Tm is 60° C. In a more preferred embodiment, the Tm is 65° C. In a specific embodiment, "high stringency"

Two "complementary" sequences bind through Watson-Crick base pairing. Two nucleic acid sequences are "substantially" complementary when their sequences are substantially complementary to hybridize. Therefore, one nucleic acid sequence need not reflect the exact sequence of the other nucleic acid. In general, "substantially complementary" is meant that one mismatch is tolerable in every about 10 base pairs of the sequences.

In the context of the present invention, two nucleic acid sequences are "substantially homologous" when at least about 75%, and most preferably at least about 90 or 95%) of the nucleotides match over the defined length of the DNA sequences, as determined by sequence comparison algorithms, such as BLAST, DNA Strider, etc. An example of such a sequence is an allelic or species variant of the specific genes of the invention. Sequences that are substantially homologous can be identified by comparing the sequences using standard software available in sequence data banks, or in a Southern hybridization experiment under, for example, stringent conditions as defined for that particular system. Said substantially homologous single-stranded or double-stranded donor DNA are aimed at undergoing homologous recombination/replacement with targeted dsDNA fragment.

Oligonucleotides according to the invention may have a native phosphodiester backbone or may comprise other backbone chemical groups or mixtures of chemical groups. Oligonucleotides may also have sugar mimetics such as cyclobutyls or other carbocyclics or hexitol in place of the pentofuranosyl group. Specific non-limiting examples of modified oligonucleotide backbones envisioned for this invention include oligonucleotides that contain phosphorothioates, methylphosphonates, phosphoramidate, morpholino nucleic acid, 2'-O,4'-C methylene bridged locked nucleic acid (LNA, Koshkin and Wengel, 1998), peptide nucleic acid (PNA), and other short chain alkyl, or cycloalkyl intersugar linkages or short chain heteroatomic or heterocyclic intrasugar linkages. U.S. Pat. No. 5,677,437 describes heteroaromatic oligonucleoside linkages. Nitrogen linkers or groups containing nitrogen can also be used to prepare oligonucleotide mimics (U.S. Pat. Nos. 5,792,844 and 5,783,682). U.S. Pat. No. 5,637,684 describes phosphoramidate and phosphorothioamidate oligomeric compounds. Also envisioned are oligonucleotides having morpholino backbone structures (U.S. Pat. No. 5,034,506). In other embodiments, such as the peptide-nucleic acid (PNA) backbone, the phosphodiester backbone of the oligonucleotide may be replaced with a polyamide backbone, the bases being bound directly or indirectly to the aza nitrogen atoms of the polyamide backbone (Nielsen et al., 1991). Other synthetic oligonucleotides may contain substituted sugar moieties comprising one of the following at the 2' position: OH, SH, SCH3, F, OCN, OCH2CH2OCH3,O(CH2)nNH2 or O(CH2)nCH3 where n is from 1 to about 10; C1 to C10 lower alkyl, substituted lower alkyl, alkaryl or aralkyl; Cl; Br; CN; CF3; OCF3; O-; S-, or N-alkyl; O-, S-, or N-alkenyl; SOCH3; SO2CH3; ONO2; NO2; N3; NH2; heterocycloalkyl; heterocycloalkaryl; aminoalkylamino; polyalkylamino; substitued silyl; or a group for improving the pharmacodynamic properties of an oligonucleotide, and other substituents having similar properties. Nucleobase other than adenine, cytosine, guanine, thymine and uracil, such as C5-methylcytosine, pseudoisocytosine, C5-propynyluracil, N7-deazaguanine, N7-glycosylated guanine, etc., may be used in an oligonucleotide.

The term "segment" as used in the expression "a nucleic acid segment" has its conventional meaning and describes a fragment or portion of a nucleic acid sequence.

The expressions "amplification" or "amplified" as used herein denotes the transcription of a nucleic acid sequence, for instance by PCR.

Throughout the specification, the term PCR whenever used is intended to any suitable method allowing the one skilled in the art to achieve nucleic acid replication.

The "third strand oligonucleotide" or "triple helix-forming oligonucleotide" (TFO) is a synthetic or isolated oligonucleotide capable of specifically binding to a predetermined binding region of a double-stranded native nucleic acid molecule to form a triple helix structure. The third strand may bind solely to one strand of the native nucleic acid molecule, or may bind to both strands at different points along its length.

The predetermined target region of the double-stranded nucleic acid may be in or adjacent to a gene, mRNA synthesis or processing region, or other nucleic acid region that it is desirable to replace by homologous recombination.

According to the invention, the predetermined target region of the double-stranded nucleic acid may be remote from the nucleic acid region that it is desirable to replace, owing to the non covalent attachment of the donor nucleic acid and the TFO.

Preferably, the TFO is a single-stranded DNA molecule of between 7 and about 50, most preferably between 10 about 30 nucleotides in length. The base composition can be homopurine, homopyrimidine, or mixtures of the two. The third strand binding code and preferred conditions under which a triple-helix will form are well known to those skilled in the art. In that respect, it may be referred to Sun et al. (1993, 1996).

The third strand needs not be perfectly complementary to the duplex, but may be substantially complementary.

The third strand oligonucleotide may also incorporate one or more modified bases if such is necessary or desirable to improve third strand binding. Examples of modified base design and the bases so designed are found in the literature (Sun et al., 1993 and 1996).

If it is desired to protect the oligonucleotide from nucleases resident in the target cells, the oligonucleotide may be modified with one or more protective groups. In a preferred embodiment, the 3' and 5' ends may be capped with a number of chemical groups known to one of ordinary skill, such as alkylamines, acridine, cholesterol, etc.

The binding of the TFO to its target sequence and the formation of a triple helix should greatly boost the homology research between the donor and the nature nucleic acid fragments and enhance the stability of the intermediate RecA-mediated complex and D-loop formation so as to induce homologous recombination at the target region of the native nucleic acid.

The "native nucleic acid" is the genomic nucleic acid to which the third strand oligonucleotide binds and that undergoes recombination. The native nucleic acid may be chromosomal or extrachromosomal. Examples of extrachromosomal DNA are well known, and include mitochondrial and episomal DNA, plasmids and chloroplasts.

In the context of the present invention, a "donor nucleic acid" is intended for an oligonucleotide which is a natural or a modified oligonucleotide (ODN), a RNA-DNA chimeric oligonucleotide (RDO), or a DNA fragment, either single- or double-stranded, or a PCR amplified ssDNA or dsDNA fragment. A fully double-stranded donor DNA is advantageous since it might provide an increased stability, dsDNA fragments being expected to be more resistant than ssDNA to nuclease degradation in vivo.

The sequence of the donor nucleic acid is substantially homologous to the native nucleic acid region which is to be replaced by homologous recombination.

The differences in base sequences between the donor nucleic acid and the targeted region it is desired to replace are base changes, deletions of bases or insertions of bases, nucleotide repeats, or a combination of these, chosen to accomplish the desired genetic and phenotypic change. Nucleic acid segments may be added according to the present invention. Such segments include a gene, a part of a gene, a gene control region, an intron, a splice junction, a transposable element, a site specific recombination sequence, and combinations thereof.

The donor nucleic acid strands, whether single- or double-stranded, may be gene sized, or greater or smaller. Preferably, they are at least about 40 bases in length, preferably between about 40 and about 1,000,000 bases in length. Most preferably, the lengths are between about 40 and about 3,000 bases.

Short donor nucleic acids (with a length of not more than 100 bases) are preferably obtained by chemical synthesis.

Larger donor nucleic acids are preferably obtained by an amplification method, e.g. a Polymerase Chain Reaction, including in situ PCR. In that case, amplified donor nucleic acid makes the recombination system according to the invention particularly versatile since it is not limited by the length of the donor nucleic acid.

According to the invention, it is not necessary to know the whole sequence of the target region wherein recombination is to occur, especially when it is sought to replace a mutated or otherwise modified sequence with a correct sequence.

Thus, according to a first preferred embodiment, a native sequence may be replaced with a donor nucleic acid obtained by amplification, for example by PCR, of a target region by using appropriate primers, isolation of is the amplification product and linkage of the amplification product to the TFO via Watson-Crick pairing between the amplified nucleic acid and an adapter comprising the nucleic sequence used as one of the primers.

In a second preferred embodiment, the donor nucleic acid is generated by PCR amplification using directly the adapter, linked to the TFO, as a primer. In that case, the donor nucleic acid is considered as a single-stranded DNA (ssDD).

The adapter used as a PCR primer can incorporate one or several ribonucleotide(s), for instance near its 3'-end. The PCR amplification produces a nucleic acid targeting system including a double-stranded DNA, a strand of which is covalently linked to the TFO guide via the adapter. Enzymatic, for instance ribonuclease A, or mild alkaline treatment of the nucleic acid targeting system may be useful to destroy the adapter ribonucleotide(s) thereby creating a break at the junction of the donor DNA strand with the adapter. This treatment allows to restore a non-covalent interaction between the donor DNA and the adapter.

However, an alternative embodiment wherein the nucleic acid targeting system comprises an amplified donor dsDNA, one strand of which is covalently linked to the adapter, is also within the scope of the invention.

This covalently linked strand may help to reduce exonucleolytic degradation of the Watson-Crick complementary strand which acts as a ssDNA donor. PCR generated donor DNA may be particularly useful for replacing into a first individual a defective gene, the sequence of which is not completely known with a correct copy of the gene. This can be achieved by amplifying the correct gene in a second individual and introducing the targeting system comprising the correct gene copy as the donor nucleic acid into the first individual.

The adapter segment is a single-stranded oligonucleotide, that may comprise between 4 and 120 nucleotides, preferably between 8 and 30 nucleotides.

The adapter is non-covalently linked to the donor nucleic acid through Watson-Crick base pairing via a single strand oligonucleotide with complementary sequence of the adapter sequence.

The adapter is preferably covalently attached to the TFO via a spacer which is comprised of a flexible chain.

According to the first and second preferred embodiment as regards to the donor DNA of the invention, the adapter may have the sequence of a primer or may be used as a primer, respectively, for amplifying a nucleic acid sequence and thereby obtaining a donor nucleic acid.

Spacers preferably comprised a hydrocarbon skeleton, optionnaly interrupted and/or substituted by one or more heteroatoms, e.g. oxygen, sulfur, nitrogen, or heterogroups that comprise at least one of these heteroatoms.

The molecule used for introducing the spacer into the construction of the invention thus comprises of a skeleton as defined above comprising at each end a group reactive with the phosphate groups of the oligonucleotide sequence of the third strand at one end, and the oligonucleotide sequence of the adapter at the other end.

Such molecules are well known to the skilled person.

Preferred spacer groups are polyethyleneglycol members or alternatively mixed structures comprised of polyethyleneglycol members and (oligo)nucleotides.

When the spacer is composed of a polyethylene glycol chain, it is preferred that the length of the chain is at least of 3, preferably of 6 ethylene oxide units.

The instant invention provides a method for effecting an homologous recombination between a native double-stranded nucleic acid segment in a cell and a donor nucleic acid segment introduced into the cell, which method comprises the steps consisting of:

a) introducing into a cell a nucleic acid targeting system comprising:
  (i) a third strand oligonucleotide which comprises a base sequence capable of forming a triple helix at a binding region on one or both strands of a native nucleic acid segment,
  (ii) a donor nucleic acid, comprising a nucleic acid sequence substantially homologous to the native nucleic acid segment so that the donor sequence is capable of undergoing homologous recombination with the native sequence at the target region,
  (iii) an adapter segment comprising an oligonucleotide sequence able to bind at least a portion of said donor nucleic acid through Watson-Crick base pairing, the adapter segment being linked to said third strand oligonucleotide,
b) allowing the third strand oligonucleotide to bind to the native nucleic acid segment to form a triple helix nucleic acid, thereby inducing homologous recombination at the native nucleic acid segment target region; and c) allowing homologous recombination to occur between the native and donor nucleic acid segments.

The method of the invention allows a substantially efficiency of the recombination by enhancing formation of the Recombinase (e.g RecA)-mediated D-loop.

Preferably, said donor nucleic acid is selected from the group consisting of a double-stranded nucleic acid, a substantially complementary pair of single stranded nucleic acids and a single stranded nucleic acid.

The donor nucleic acid may be either synthetic or a PCR amplified product. In this case, the method of the invention comprises the steps consisting of:

a) providing a pair of primers complementary of the 5' and 3' ends of a double-stranded first native nucleic acid sequence;

b) amplifying said first native nucleic acid sequence, c) isolating the amplification product thus obtained;

d) annealing the amplification product with an adapter segment comprising an oligonucleotide sequence able to bind at least a portion of the nucleotide sequence of said amplified nucleic acid through Watson-Crick base pairing, said adapter segment being linked to a third strand oligonucleotide which comprises a base sequence capable of forming a triple helix at a binding region on one or both strands of a second native nucleic acid segment, thereby providing a nucleic acid targeting system comprising:
  i) said third strand oligonucleotide,
  ii) said amplification product as a donor nucleic acid segment, and
  iii) said adapter segment bound to said donor nucleic acid segment through Watson-Crick base pairing;

e) introducing said nucleic acid targeting system into a cell comprising a second native nucleic acid different from the first native nucleic acid;

f) allowing the third strand oligonucleotide to bind to the second native nucleic acid segment to form a triple helix nucleic acid, thereby inducing homologous recombination at the second native nucleic acid segment target region; and g) allowing homologous recombination to occur between the second native and donor nucleic acid segments.

According to the invention, the donor nucleic acid can be amplified while using the adapter as a PCR primer. The method for effecting homologous recombination therefore comprises the steps consisting of:

a) providing a pair of primers complementary to the 5' and 3' ends of a double-stranded first native nucleic acid sequence, wherein one of the primers is an adapter segment linked to a third strand oligonucleotide that comprises a base sequence capable of forming a triple helix at a binding region on one or both strands of a second double-stranded native nucleic acid segment;

b) amplifying said first native nucleic acid sequence, c) isolating the amplification product thus obtained, thereby providing a nucleic acid targeting system comprising:
  i) said third strand oligonucleotide,
  ii) said amplification product as a donor nucleic acid segment, and
  iii) said adapter segment bound to a strand of said donor nucleic acid segment through Watson-Crick base pairing;

d) introducing said nucleic acid targeting system into a cell comprising a second native nucleic acid different from the first native nucleic acid;

e) allowing the nucleotide to bind to the second native nucleic acid segment to form a triple helix nucleic acid, thereby inducing homologous recombination at the second native nucleic acid segment target region; and f) allowing homologous recombination to occur between the second native and donor nucleic acid segments.

Preferably the amplified donor is a double-stranded DNA that interacts with the adapter through Watson-Crick base pairing only. Thus, the invention also relates to a method for effecting homologous recombination comprising the steps consisting of:

a) providing a pair of primers complementary to the 5' and 3' ends of a first double-stranded native nucleic acid sequence, wherein one of the primers is a modified adapter segment which contains one or several ribonucleotide(s) at its 3'-end, wherein said adapter segment is linked to a third strand oligonucleotide which comprises a base sequence capable of forming a triple helix at a binding region on one or both strands of a second double-stranded native nucleic acid segment;

b) amplifying said first native nucleic acid sequence, c) isolating the amplification product thus obtained, d) treating the isolated amplification product in conditions sufficient to allow destruction of said ribonucleotide thereby providing a nucleic acid targeting system comprising:

i) said third strand oligonucleotide, ii) said amplification product as a donor nucleic acid segment, and iii) said adapter segment bound to said donor nucleic acid segment through Watson-Crick base pairing;

e) introducing said nucleic acid targeting system into a cell comprising a second native nucleic acid different from the first native nucleic acid;

f) allowing the nucleotide to bind to the second native nucleic acid segment to form a triple helix nucleic acid, thereby inducing homologous recombination at the second native nucleic acid segment target region; and g) allowing homologous recombination to occur between the second native and donor nucleic acid segments.

Preferably, the ribonucleotide is positioned at the free end of the adapter, i.e. the side that is not covalently linked to the third strand oligonucleotide. A suitable treatment to destroy ribonucleotide includes enzymatic treatment or mild alkaline treatment. Therefore, in the latter method, step d) preferentially comprises enzymatic treatment or mild alkaline treatment.

The donor nucleic acid targeting system of the invention may be introduced into the target cell by means of any procedure known for the delivery of nucleic acids to the nucleus of cells, ex vivo, on cells in culture or removed from an animal or a patient, or in vivo.

Ex vivo introduction may be performed by any standard method well known by one skilled in the art, e.g. transfection, electroporation, microinjection, transduction, cell fusion, DEAE dextran, calcium phosphate precipitation, or use of a gene gun (see for instance Wu et al., 1992; Wu et al, 1988).

The donor nucleic acid targeting system can also be introduced ex vivo or in vivo by lipofection. In certain embodiments, the use of liposomes and/or nanoparticles is contemplated for the introduction of the donor nucleic acid targeting system into host cells.

Nanocapsules can generally entrap compounds in a stable and reproducible way. To avoid side effects due to intracellular polmeric overloading, such ultrafine particles (sized around 0.1 µm) should be designed using polymers able to be degraded in vivo. Biodegradable polyalkyl-cyanoacrylate nanoparticles that meet these requirements are contemplated for use in the present invention, and such particles may be are easily made.

Liposomes are formed from phospholipids that are dispersed in an aqueous medium and spontaneously form multilamellar concentric bilayer vesicles (also termed multilamellar vesicles (MLVs)). MLVs generally have diameters of from 25 nm to 4 µm. Sonication of MLVs results in the formation of small unilamellar vesicles (SUVs) with diameters in the range of 200 to 500 Å, containing an aqueous solution in the core.

Synthetic cationic lipids designed to limit the difficulties and dangers encountered with liposome mediated introduction can be used to prepare liposomes for in vivo delivery of the targeting system of the invention (Felgner, et. al., 1987; Mackey, et al., 1988). The use of cationic lipids may promote encapsulation of negatively charged nucleic acids, and also promote fusion with negatively charged cell membranes (Felgner et al., 1989).

The method of the invention is useful for effecting mutation repair, and targeted mutagenesis at a specific-sequence site on a native nucleic acid segment, either in cells or in a living organism.

The method of the invention is namely useful for correcting a native nucleic acid containing one or more mutations by homologous recombination.

The mutations may consist of base changes, deletions, insertions, nucleotide repeats, and combinations thereof.

The method is particularly useful for causing an alteration in the native nucleic acid by the homologous recombination.

The alteration may be caused in a segment selected from the group consisting of a gene, a part of a gene, a gene control region, an intron, a splice junction, a transposable element, a site specific recombination sequence, and combinations thereof.

The method of the invention is particularly useful for therapeutical purposes. For example, if a targeted nucleic acid region contains base changes, deletions or additions of bases which cause an inherited or somatic genetic disorder, then the donor nucleic acid can provide a normal gene by replacing the defective nucleic acid to correct that disorder. If the targeted nucleic acid region is one which confers inherited or acquitted susceptibility to a genetic disorder (e.g. cancer), the donor nucleic acid can reverse that susceptibility.

A preferred therapeutic use of the methods and compositions of the invention are in ex vivo therapies where third strand oligonucleotide and donor nucleic acid can be introduced into target cells outside the body.

Diseases amenable to ex vivo treatment include white blood cell diseases such as leukemias and red blood cell diseases such as sickle-cell anemia and α/β-thalassemia. The individual steps used in such therapies are well known to one of ordinary skill. For example, such steps include removing bone marrow from the patient, treating it with a targeting system according to the invention to stimulate homologous recombination, and after selection returning the treated bone marrow to the patient's body. Therapies that remove, treat and return the patient's own bone marrow are called autologous bone marrow transplants (ABMT).

The method of the invention may further be used for effecting gene alteration or mutation repair in vivo and for developing transgenic animals.

The invention thus relates to a method for effecting in vivo or ex vivo gene alteration or mutation repair at a specific-sequence site on a native DNA, comprising:

a) introducing into a cell a nucleic acid targeting system comprising:

(i) a third strand oligonucleotide which comprises a base sequence capable of forming a triple helix at a binding region on one or both strands of a native nucleic acid segment, (ii) a donor nucleic acid, comprising a nucleic acid sequence substantially homologous to the native nucleic acid segment such that the donor sequence is capable of undergoing homologous recombination with the native sequence at the target region, (iii) an adapter segment comprising an oligonucleotide sequence able to bind at least a portion of said donor nucleic acid through Watson-Crick base pairing, the adapter segment being linked to said third strand oligonucleotide, b) allowing the oligonucleotide to bind to the native nucleic acid segment to form a triple helix nucleic acid, thereby inducing homologous recombination at the native nucleic acid segment target region; and c) allowing homologous recombination to occur between the native and donor nucleic acid segments, thereby performing that gene alteration or mutation repair.

In yet another aspect, the present invention provides a kit, which comprises:

i) a third strand oligonucleotide which comprises a base sequence capable of forming a triple helix at a binding region on one or both strands of a native nucleic acid segment;

ii) a donor nucleic acid, comprising a nucleic acid sequence substantially homologous to the native nucleic acid segment so that the donor sequence is capable of undergoing homologous recombination with the native sequence at the target region;

iii) an adapter segment comprising an oligonucleotide sequence able to bind at least a portion of said donor nucleic acid through Watson-Crick base pairing, the adapter segment being linked to said third strand oligonucleotide, The present methods and kits are useful in research and therapeutic applications where recombination at a specific site is desired.

The present invention is also useful in plant agriculture.

The present invention is also useful as a research tool, for example for studying the function of genes by introducing mutations at specific positions of said gene In plant agriculture, the methods and kits of the invention may be used to, for example, for increasing the protein nutrition of grains by replacing storage protein genes with genes which retain their ability to pack into seeds but provide proteins with more limiting essential aminoacids such as lysine and tryptophan; adding genes with new functions such as insect resistance; and increasing the expression of genes with useful properties.

The invention will be further understood in view of the following examples and the annexed figures wherein:

EXAMPLE 1

Design and Description of Targeting Systems According to the Invention

A GOREC system is designed as a kit composed of two functional modules, a "guide" and a "recombinant DNA" fragment, in order to achieve site-specific recombination/mutagenesis (FIG. 1). Guide module is made of three covalently linked elements: a triple helix-forming oligonucleotide (TFO); a synthetic spacer; and an oligonucleotide adapter. In this study, a single-stranded recombinant DNA fragment which shares sequence homology with a target DNA sequence in the vicinity of the TFO binding site except at the mutation site was used. The two modules are linked together through Watson-Crick base pairing between the 12-nt adapter and the complementary sequence at the 5'-end of recombinant DNA. This modular design was motivated by two reasons: 1) the non-covalent attachment of recombinant DNA to the guide sequence might facilitate the exchange step of recombination, and most importantly, it should reduce the risk of unexpected mutation due to the TFO (which is not a homologous DNA fragment), as compared to a covalent attachment; 2) the 12-nt adapter can be used as one of the primers to obtain recombinant DNA by PCR amplification.

Sequence-specific dsDNA recognition by TFO via stable triple helix formation under physiological conditions at neutral pH and 37° C. is a prerequisite in the GO REC approach. As depicted in FIG. 1, an 18-bp oligopyrimidine•oligopurine sequence which has been chosen as a target and cloned into a DNA plasmid (Y0Gorec) in the promoter region of yeast URA3 gene. The plasmid Y0Gorec (6922 bp) was constructed by introducing a 42-bp sequence, containing the 18-bp oligopyrimidine-oligopurine sequence which is a target for TFO's, five codons after the ATG initiation codon of the URA3 gene in plasmid YEpURA3.22. Supercoiled duplex DNA was purified on a cesium chloride gradient.

A pyrimidine-motif of triplex can be formed upon binding an 18-nt oligopyrimidine (TFOØ) under acidic condition. Such a triplex is not expected to be stable at neutral pH. As an alternative, a mixed motif where a 17-nt TFO (TFO1) composed of 5-propynyl-deoxyuraciles (u), 5-methyl-deoxycytosines (o), deoxyguanines and 7-deazadeoxyguanines (g) as well as a 5'-tethered acridine derivative was chosen to form a stable triplex at neutral pH. It has been shown previously that 1) the replacement of six consecutive cytosines by guanines relieves the pH-dependence of triplex formation, 2) the partial substitution of guanines by 7-deaza-guanines prevents intermolecular G4-quadruple formation between oligomers with $G_6$ tracts, 3) the 5-propynyl-uraciles, 5-methyl-cytosines confer enhanced binding of TFO, and 4) the attachment of a dsDNA intercalator, such as acridine, at the 5'-end of TFO further stabilizes the triplex.

The two TFOs were covalently attached to a linker which is made of a tri- or hexaethyleneglycol spacer, (S or L respectively) and a 12-nt oligonucleotide (adapter) as represented in FIG. 1.

Table 1 hereunder summarizes the composition and nomenclature of different GOREC systems used herein.

TABLE 1

| Name | Guide | Spacer | Recombinant DNA |
|---|---|---|---|
| TFO1-S + R | TFO1 | S | R |
| TFO1-L + R | TFO1 | L | R |
| TFO1-S + M | TFO1 | S | M |
| TFOØ-S + R | TFOØ | S | R |
| TFOØ-S + M | TFOØ | S | M |

EXAMPLE 2

Thermal Stability and Binding Affinity of the Targeting Systems of Example 1

Thermal Stability

DNA melting experiments by UV spectrophotometry were first carried out to assess the thermal stability of triple helix formation by TFOs. A hairpin duplex containing the 18-bp oligopyrimidine•-oligopurine target sequence (5'-CGTCTAGAAAAGAAAAGGGGGGATACGC-$T_4$-GCGTATCCCCCCTTTTCTTTTCTAGACG-3',) (SEQ ID n°1-T4-SEQ ID n°2) as represented in FIG. 1 was used.

Thermal denaturation and renaturation studies of duplexes and triplexes were carried out on a Kontron Uvikon 940 spectrophotometer with 1 cm optical path length quartz cuvettes. The cell holder was thermoregulated by circulating liquid composed of 80% water/20% ethylene glycol (v/v). Samples were cooled from 80° C. to 0° C. and heated back to 80° C. at 0.1–0.15° C./min (as indicated) with absorption readings at 260 and 400 nm taken every 1° C. Samples were kept for an additional 30 min at the lowest and highest temperature. All samples were prepared in a buffer containing 20 mM sodium cacodylate, pH 7.2, 50 mM NaCl and 5 mM $MgCl_2$. For melting temperature (Tm) analysis, the baseline drift was corrected by substracting absorption at 400 nm from that at 260 nm. The melting curve was obtained by plotting the corrected absorbance at 260 nm versus temperature (° C.). The maximum of the first derivative of melting curve (δA/δT) was taken as an estimation of Tm value. A hairpin duplex containing the 18-bp oligopyrimidine-oligopurine target sequence (5'-CGTCTAGAAAAGAAAAGGGGGATACGC-$T_4$-GCGTATCCCCCCTTTTCTTTTCTAGACG-3', designated as 18YR) (SEQ ID n°1-T4-SEQ ID n°2) was used.

Figure 2:
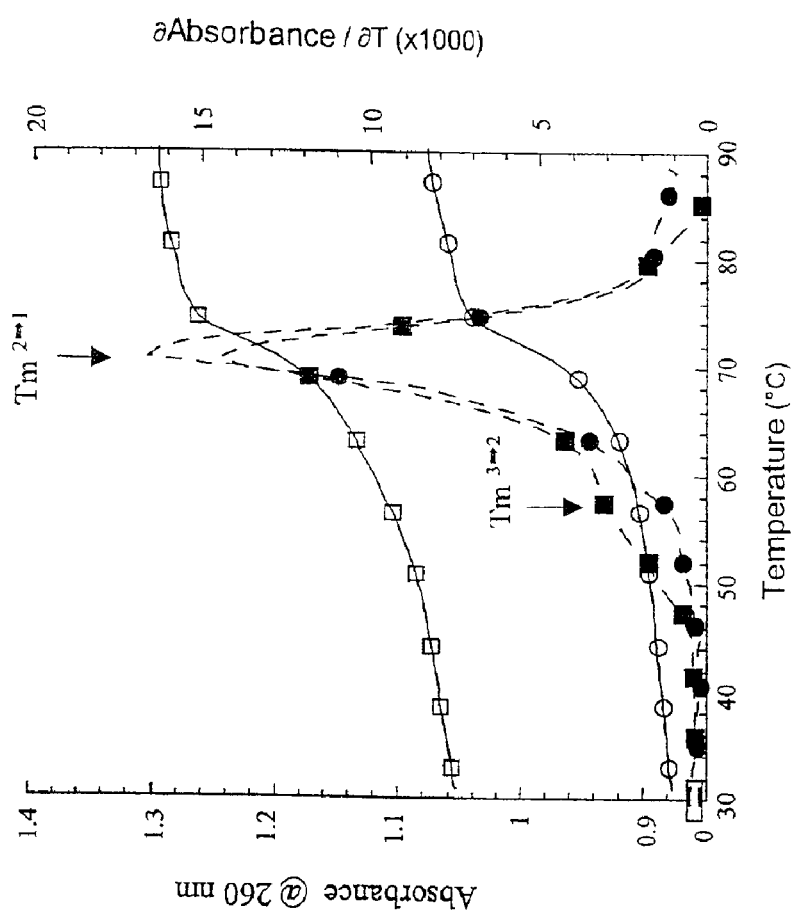
FIG. 2 represents the melting curve of 18YR+TFO1 (solid line with open squares) and its first derivative (dashed line with filled squares). The melting curve of duplex 18YR alone (solid line with open circles) alone is also shown. The Tm values of the triplex (18YR+TFO1) and the duplex (18YR) are indicated by arrows.

FIG. 2 shows that melting curves of the TFO and the target double helix in 20 mM cacodylate buffer (pH 7.2) containing 50 mM NaCl and 5 mM $MgCl_2$. A bi-phasic melting curve was observed with the sample containing 1 $\mu M$ duplex 18YR and 1.5 $\mu M$ TFO1. The transition occurring at high temperature (70° C.) was identical to that observed for the duplex alone, therefore it was attributed to duplex⇌single strand transition. The transition at lower temperature was assigned to triplex⇌duplex+TFO transition, since the TFO1 alone did not exhibit any melting profile. The melting temperature ($Tm^{3 \to 2}$) of the triplex formed by TFO1 and 18YR was about 56° C. as measured by the first derivative of the melting curve. Though as anticipated, the non-modified oligopyrimidine TFOØ did not form a stable triple helix under these conditions, triplex formation by TFOØ was observed at pH 6.2 ($Tm^{3 \to 2}$=28° C.). When the adapter was linked to TFO through a triethyleneglycol (S) spacer and a 40-nt ssDNA fragment (R) were appended to the guide module (TFO1-S or TFO1-S+R, respectively), the $Tm^{3 \to 2}$ values were slightly decreased by 4–6° C. It is known that a dangling end on the third strand destabilizes triple helix, probably due to negative charge repulsion (Cheng et al., 1994). The melting temperature ($Tm^{2 \to 1}$) of the 12-bp duplex formed between the 12-nt adapter and the R fragment was about 64° C. under the same conditions.

Binding Affinity

Binding affinity of the GO REC system to target dsDNA was evaluated by gel retardation and by restriction enzyme assay in solution.

DNA Labelling. The short target duplex (18YR) or the oligopyrimidine triplex-forming oligonucleotide (TFOØ and TFOØ-S), as well as the recombinant (R) and control (M) fragments (see FIG. 1) were 5' end-labeled with [$\gamma^{32}P$] ATP (Amersham Arlington Heights, Ill.) by T4 polynucleotide kinase (New England Biolabs, Beverly, Mass.). TFO1-S or TFO1-L was 3'-labelled by calf thymus terminal transferase (Boehringer Mannheim). Unincorporated radioactivity was eliminated using the Centri Spin-20 columns from Princeton Separation Inc. Specific activity was estimated by precipitation of aliquots with ice-cold 10% TCA and counting the radioactivity. When needed the labeled oligonucleotides where diluted with unlabelled oligonucleotides to adjust the specific activity.

Gel retardation assay. 20 nM radiolabeled duplex 18YR were titrated by TFOs in the concentration range of 0.1 to 3 $\mu M$ and incubated in 50 mM HEPES buffer (pH 7.2) containing 50 mM NaCl and 5 mM $MgCl_2$ at 37° C. for 1 hour, then loaded on a non denaturing 10% acrylamide gel (19/1 mono/bis acrylamide). Electrophoresis was performed at 4 Watt for three hours in 50 mM HEPES buffer (pH 7.2) in the presence of 5 mM $MgCl_2$ at 4° C. The gel was then dried and quantified with a phosphorimager The quantification of each band intensity (triplex, duplex and TFO) allowed the calculation of the apparent triple helix dissociation constant $K_D$ according to a simple two-state model.

Joint Molecule Assays. Joint molecules were formed by 10 minutes preincubation at 37° C., using 0.5 $\mu M$ labeled ssDNA in a reaction mixture containing 20 mM tris-HCl and 12.5 mM $MgCl_2$ (D-loop buffer) in the absence or in the presence of 15 $\mu M$ RecA protein, 0.3 mM ATPγs and 1.1 mM ADP. Y0Gorec plasmid (0.05 $\mu M$) was added at time zero. The final reaction volume was 10 $\mu l$. At the indicated time, one volume of stop buffer, containing 1% SDS and 20 mM EDTA, was added to the reaction mixture. The samples were separated at 4° C. by a 2 hours electrophoresis (150 mA) on a 0.8% agarose gel using tris-borate buffer (pH 8) supplemented with 5 mM $MgCl_2$. The gel was dried and quantified with a phosphorimager.

Enzyme Assays. Various concentration of TFOs were incubated for 1 hour with 0.25 $\mu g$ the PfIm I-linearized Y0Gorec plasmid to form complex at 37° C. Cleavage reaction was triggered by addition of 20 units of Xba I, allowed to process for 15 minutes, and then stopped by addition of 0.1 M EDTA. The digested products were loaded on an ethidium bromide stained 1% agarose gel in 1×TBE buffer.

Joint molecules were directly treated by the enzymes when RecA was absent. In reactions catalyzed by RecA protein, the protein was eliminated by adding EDTA and filtrating on a centrifugal concentrator Nanosep 100K from Pall Filtron with washing in D-loop buffer. Joint molecules were either treated with different amounts of nuclease P1 (Boehringer Mannhein) for 15 min. at 37° C., in a buffer containing 20 mM Tris-HCl, 12.5 mM $MgCl_2$ and 5 mM $ZnCl_2$ or incubated with 10 units of XbaI. The extent of enzyme digestion was measured at 150 mA on a 0.8% agarose gel by a 2 hours electrophoresis at 4° C. in Tris-borate buffer (pH 8) supplemented with 5 mM $MgCl_2$. The gel was dried and quantified with a phosphorimager.

Figure 3A:
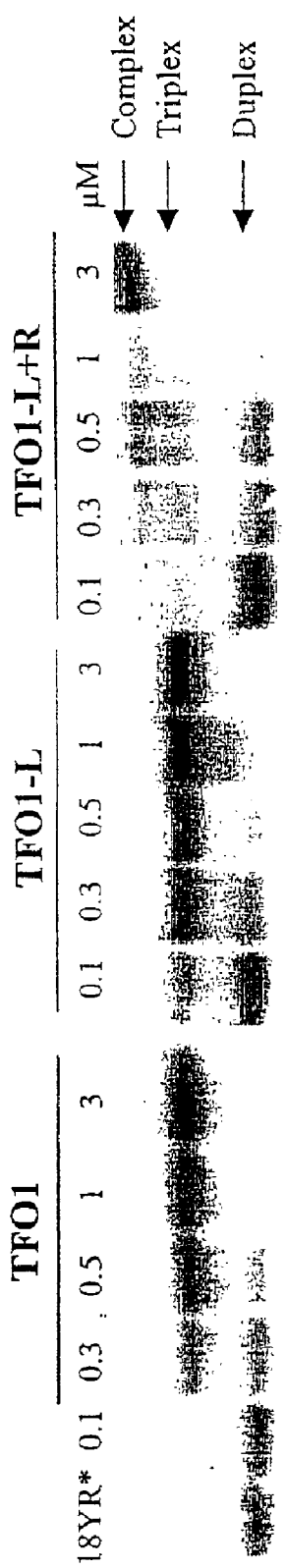
FIG. 3A represents a gel retardation pattern of different GOREC. Increasing concentrations of the guide (TFO1), the guide-linker (TFO1-L) and the GOREC system (TFO1-L+R) were added to the 5'-labeled duplex (18YR*) (panel A) or to the Y0Gorec plasmid DNA (panel B).

Triple helix formation could be easily detected by altered mobility of radiolabeled duplex or TFO in non denaturing acrylamide gel electrophoresis. As the concentration of TFOs increased, the migration of labelled duplex was retarded in a concentration-dependent manner, indicative of triple helix formation as represented in FIG. 3A. Quantification of gel retardation as a function of TFOs' concentration provided the dissociation equilibrium constant $K_D$ of the GO REC system as represented in table 2 hereunder.

TABLE 2

|  | $K_D$ ($\mu M$)[a] | $IC_{50}$ ($\mu M$)[b] |
| --- | --- | --- |
| TFO1 | 0.3 | 0.2 |
| TFOØ-s | NB | NI |
| TFO1-S | 0.3 | 0.5 |
| TFO1-S + R | 0.7 | 0.8 |
| TFO1-L | 0.4 | 0.2 |
| TFO1-L + R | 0.5 | 0.3 |

It was observed that the binding constant ($K_D$) of TFO1 was about 0.3 $\mu M$. The covalent attachment of a 12-nt adapter to TFO1 did not affect much the binding affinity whatever a short (triethyleneglycol) or a long (hexaethyleneglycol) spacer was used (TFO1-S or TFO1-L, respectively). However, the attachment of a 40-nt ssDNA fragment (R) caused about 2-fold decrease of binding affinity for the GO REC system with a short spacer (TFO1-L+R) whereas the loss was less pronounced with a long spacer (TFO1-S+R). pointed out again that the presence of a dangling end oligonucleotide was, to some extent, detrimental to the binding of TFO, especially when the length of spacer was short.

Figure 3B:
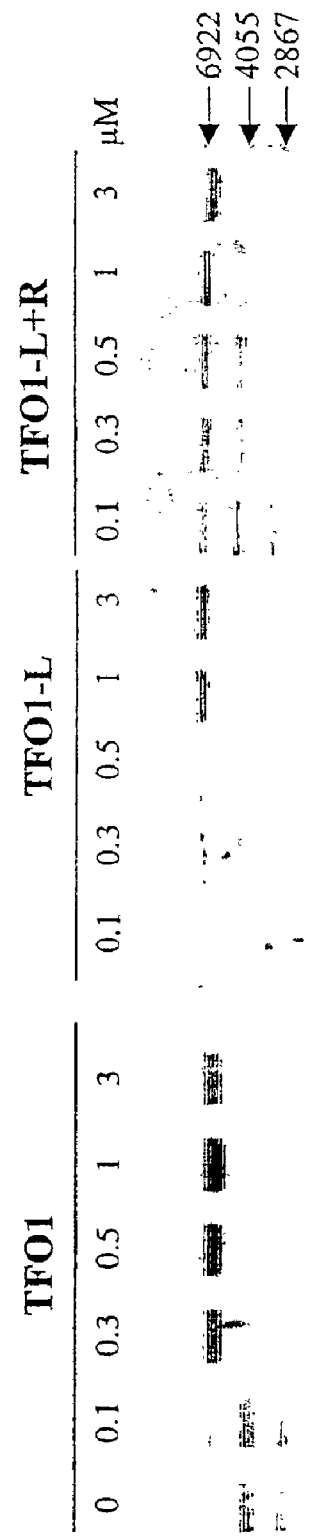
FIG. 3B: Xba I restriction enzyme assays of the same systems.

In parallel with gel retardation experiments, another assay based on the inhibition of restriction enzyme activity in solution was carried out. The binding site of Xba I nuclease overlaps that of TFO, therefore triple helix formation prevents the binding of the enzyme, and thus inhibits its DNA cleaving activity. The 6922-bp plasmid Y0Gorec was first linearized by the restriction enzyme Pflm I. The subsequent digestion by Xba I generates two DNA fragments of 2867-bp and 4055-bp. FIG. 3B shows that the cleavage of the linearized plasmid by Xba I was inhibited when the concentration of TFOs was increased. The concentration required to achieve 50% inhibition of Xba I digestion ($IC_{50}$) was deduced from the gel quantification (table 2). It reflects the binding affinity of TFOs, provided the enzyme cutting was not a limiting step. It is interesting to note that, in general, the $IC_{50}$ values correlated quite well with the $K_D$ values obtained by gel retardation experiments. A similar trend of binding affinity for various GOREC systems as regard to the effect of linker length and of dangling end was observed using both gel retardation and enzyme inhibition assays (table 2).

It is thereby noted that the affinities of the TFO of the various targeting systems are consistent and within submicromolar concentration range under near physiological conditions at 37° C.

EXAMPLE 3

Kinetics Studies of the Targeting Systems of Example 1

Kinetic studies were performed on a BIAcore2000™ apparatus (BIAcore AB, Uppsala, Sweden). The fluidic system consists of four detection surfaces located in separate flow cells that can be addressed either individually or serially in a multichannel mode. The dsDNA or ssDNA target was immobilized on a dextran CM5 sensor chip via a biotin tag which was captured by a streptavidin previously immobilized on the same chip according to the instruction provided by manufacturer. The experiments were carried out at 37° C. in 20 mM cacodylate buffer (pH 7) containing 50 mM NaCl and 5 mM $MgCl_2$. The flow rate was set at 10 or 50 µl/minute for triplex or duplex measurements, respectively. The regeneration was done by injection of a mixture containing 2 M urea, 20% ethanol and 0.05% SDS for 30 seconds. One flow cell with non specific dsDNA or ssDNA was used as a reference to correct either bulk refractive index contributions which are related to differences in the composition of injected samples as compared to running buffer, or baseline drift during course of data collection. The corrected sensorgrams were analyzed by using BIAevaluation software (version 2.0). The validity of rate constants was confirmed by comparing the calculated $K_D$ ($k_{diss}/k_{ass}$) at Tm with that determined in DNA thermal denaturation experiments.

Results

A hairpin dsDNA fragment containing the 18-bp oligopyrimidine•oligopurine target sequence (5'-CGTCTAGAAAAGAAAAGGGGGATACGC-$T_4$-GCGTATCCCCCCTTTTCTTTTCTAGACG-$T_7$-3'-biotin) (SEQ ID n°1-T4-SEQ ID n°2-T7-3'-biotin) was anchored via a biotin tag which was captured by a streptavidin previously immobilized on the sensor chip. The real-time association and dissociation of TFO were monitored and recorded by BIAcore. As expected, the association process was concentration-dependent whereas the dissociation was concentration-independent. All sensorgrams could be analyzed according to a simple two-state model. Table 3 shows the rate constants of triple helix formation at 37° C.

TABLE 3

|  | $k_{diss}$ ($10^{-4}s^{-1}$) | $k_{ass}$ ($M^{-1}.S^{-1}$) | $K_D$ (µM) |
| --- | --- | --- | --- |
| TFO1 | 2.5 ± 0.2 | 1100 ± 26 | 0.2 |
| TFO1-L | 2.1 ± 0.4 | 812 ± 60 | 0.3 |
| TFO1-L + R | 3.1 ± 0.2 | 627 ± 31 | 0.5 |

It is noted that the dissociation rate constant ($k_{diss}$) was slightly increased, whereas the association rate constant ($k_{ass}$) was also decreased in the presence of a tethered 40-nt recombinant oligonucleotide (TFO1-I+R). This observation can again be explained by charge repulsion between the target dsDNA and the dangling tail of the third strand oligonucleotide. Under these conditions, the lifetime ($1/k_{diss}$) of triplexes was about one hour. It should be noted that the dissociation equilibrium constants ($K_D$) calculated as the ratio of $k_{diss}$ over $k_{ass}$ were consistent with those obtained in binding assays (see above).

Under the same conditions, kinetic experiments were performed by BIAcore to measure the rate constants of the 12-bp duplex (5'-GCCGTGGCCAGC-3'/3'-GCGCACCGGTCG-5') (SEQ ID n°3/SEQ ID n°4) formed between the 5'-end of 40Y and the 12-nt adapter. As usual, a biotinylated oligonucleotide (biotin-3'-$T_7$-GCGCACCGGTCG-5') (biotin-3'-T7-SEQ ID n°4) was captured on the sensor chip to reach 700 RU. The sensorgrams of the binding of the 12-nt oligonucleotide with complementary sequence (5'-GCCGTGGCCAGC-3'; SEQ ID n°3) was analyzed according to a two-state model. The association rate constant of this 12-bp duplex was about $4 \times 10^4$ $M^{-1}.s^{-1}$ (36-fold higher than that of triplex), whereas the duplex dissociation rate constant was about $1.7 \times 10^{-4}$ $s^{-1}$ which was slightly lower than that of the triplex. The lifetime of the duplex was about 1.6 hour.

EXAMPLE 4

Joint Molecules Formation is Stimulated by RecA Protein and Triplex Formation

The ability of various GOREC systems to form stable joints with the plasmid Y0Gorec was assessed. The plasmid Y0Gorec carries a sequence homologous to the R oligonucleotide in the vicinity of the oligopyrimidine-oligopurine sequence where the guide TFO forms an intermolecular triple helix (FIG. 1). Depending upon the incubation conditions and the presence or the absence of the RecA protein, oligonucleotides can interact with the duplex plasmid DNA and form two kinds of structures: a D-loop and/or an intermolecular triple helix. The joint molecules were detected as labeled oligonucleotides co-migrating with the circular plasmid (both open circle and supercoiled) and the nature of their junctions was further analyzed by nuclease digestion. Molecules with TFOØ-S and M sequences were used as controls as they did not form triplex at neutral pH and had no homology with the plasmid, respectively.

Figure 4B:
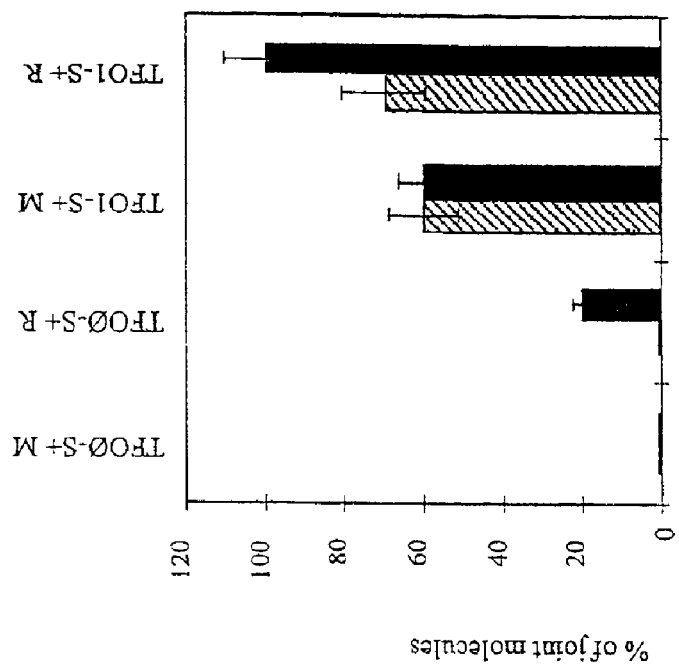
FIG. 4 represents the results of co-migration gel analysis (panel A) and quantification of joint molecules (panel B). DNAs were incubated 45 minutes in the absence (hatched boxes) or in the presence (black boxes) of RecA protein. oc: open circle; ccc: supercoiled plasmid.
Figure 4A:
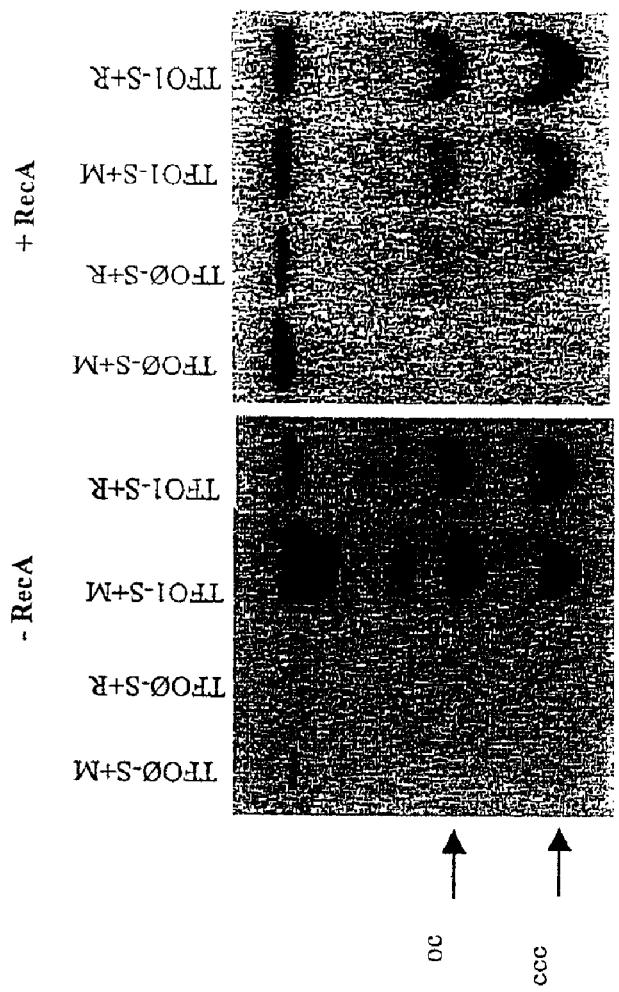

The reactions were first performed in the absence of RecA protein (FIG. 4). The joint molecule formation was not detected when the guide TFOØ-S was associated to either M or R oligonucleotides. In contrast, they were efficiently formed when the guide TFO1-S was associated with either M or R fragment. These results indicate that the presence of a DNA fragment with an homologous or heterologous sequence did not affect triple helix formation within a plasmidic DNA. In addition, the absence of joint molecule formation with the TFOØ-S+R (which carries the recombinant DNA but cannot form triplex) confirmed that the joint molecules formed with the plasmid under these conditions were only due to triplex formation.

In vitro, the RecA protein has been shown to promote formation of joint molecules between oligonucleotides and homologous duplexes (35). The efficiency of the reaction depends upon the size of the oligonucleotide probably because RecA filaments are very unstable on short ssDNAs (36–38). Under our experimental conditions, few joint molecules were detected, after 45 minutes incubation with the TFOØ-S+R oligonucleotide and the duplex DNA (FIG. 4). These joint molecules were not formed in absence of RecA protein. The efficiency of the reaction was 5-fold stimulated when the R fragment was associated to the TFO1-S rather than the TFOØ-S oligonucleotide (FIG. 4). The formation of joint molecules between TFO1-S+M complex and duplex DNA, was not affected by the RecA protein. This result indicated that the binding of RecA protein did not significantly interfere with triplex formation. Moreover, RecA was able to enhance the formation of joint molecule between TFO1-S+R complex and duplex DNA: 100% of the complex were associated to the plasmid duplex in the reaction catalyzed by the RecA protein.

Figure 5A:
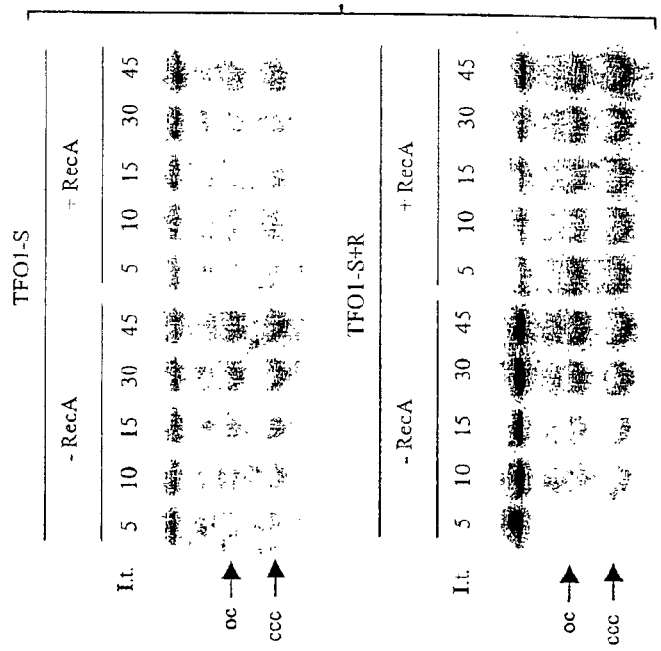
FIG. 5 represents the results of co-migration gel analysis (panel A) and quantification of kinetics of joint molecules formation (panel B). TFO1-S+R complexes (circles) and TFO1-S molecules (squares) were incubated for different times with duplex DNA in a reaction buffer containing (full lines) or not (dashed lines) the RecA protein. oc: open circle; ccc: supercoiled plasmid. I.t.: incubation time in minutes.
Figure 5B:
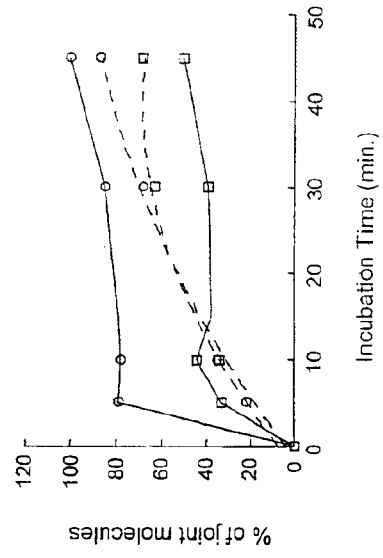

To assess the effect of the RecA protein on the formation of the joint molecule between the GOREC system (TFO1-S+R) and the Y0Gorec plasmid, the kinetics of the reactions with and without the protein were compared (FIG. 5). Similar kinetic measurements were performed with the guide TFO1-S alone, in order to estimate the contribution of the triplex formation during the reaction. The main effect of the RecA protein appears to be the acceleration of the reaction: 80% of the joint molecules were formed in five minutes with TFO1-S+R in presence of RecA whereas only 22% were detected in the absence of the protein at the same time (FIG. 5-B). The slow rate of triple helix formation in the absence of RecA protein was not due to the R recombinant oligonucleotide since the TFO1-S alone also exhibited slow kinetics of triple helix formation. All these data taken together suggest that both kind of structures, the triplex and the RecA dependant D-loop, were formed in this reaction.

EXAMPLE 5

Nature of the Junctions within the Joint Molecules

Joint molecules formed by the TFO1-S+R in the reaction stimulated by RecA protein, can result from: 1) the formation of a triple-helical structure between the guide TFO1-S and its target, and/or 2) the formation of a D-loop structure between the R recombinant DNA and the homologous sequence on the plasmid. To determine the respective contribution of the two structures, the sensitivity of the joint molecules to different enzymes whose activity is specific of different DNA structures was measured. It was found that most of the plasmids in the joint molecule formed with TFO1-S+R, were resistant to Xba I cleavage indicating the formation of the triplex structure (FIG. 6-A). As expected, joint molecules formed with TFOØ-S+R were sensitive to Xba I restriction enzyme. In D-loop structures, the ssDNA which had invaded the homologous duplex DNA to form a duplex structure became resistant to degradation by ssDNA nucleases. The R recombinant fragment was resistant to P1 exonuclease in the joint molecules formed by TFO1-S+R in presence of RecA protein. In contrast, the non homologous M sequence was sensitive to the ssDNA nuclease in the joint molecule formed by TFO1-S+M. Digestion of M fragment indicates that the protection observed in the TFO1-S+R joint molecule was not due to remaining RecA binding but rather to homology-dependent interaction with the plasmid. The TFO1-S+R joint molecule formed in absence of the RecA protein as sensitive to P1 digestion as the TFO1-S+M (data not shown). This observation indicated that triplex formation was not able to promote D-loop formation in absence of RecA protein. The two analysis of the sensitivity of joint molecules to enzymatic digestion showed that most of the joint molecules formed by TFO1-S+R in presence of RecA protein, contained both triplex and D-loop junctions.

EXAMPLE 6

Ex Vivo Assays

As an alternative to guide a synthetic single- or double-stranded donor DNA fragment which has limited length (usually less than 100-nt or 100-bp) that restrains the directed mutagenesis site in the close vicinity of the triple helix site, the donor DNA can be prepared by PCR amplification as described in this example. The main advantage of PCR prepared DNA fragment is that it extends directed mutagenesis at the site which can be several hundreds to thousands base pairs away from the triple helix site by GOREC method due to the longer length of PCR fragment. Therefore GOREC method could be applied to a large number of genes of interest because it is almost possible to find out a suitable triple helix site several hundreds base pairs around.

Figure 7:
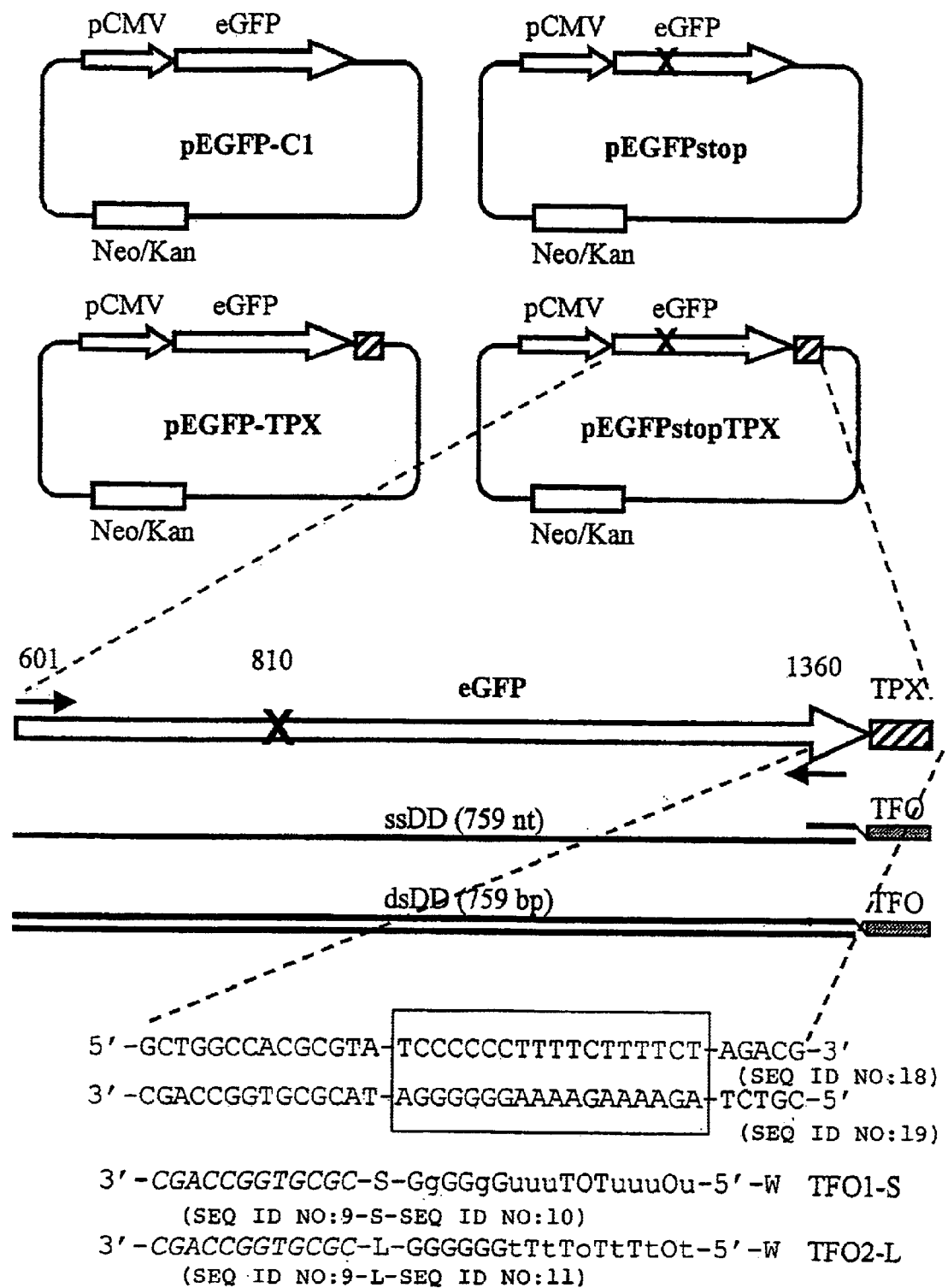
FIG. 7 describes the constructs of plasmids used in ex vivo assays in Example 6: In the construct of pEGFP-stopTPX plasmid, a stop codon was introduced at the position 810 in the eGFP gene and a site for triple helix formation (TPX) was cloned at the 3' end of eGFP. GOREC molecule is made of a triple helix-forming oligonucleotide (TFO) (SEQ ID NO:10 and SEQ ID NO:11) tethered to an adapter (SEQ ID NO:9) oligonucleotide through a linker. Two arrows indicate the primers used for the preparation of ssDD and dsDD by PCR amplification. The oligopyrimidine·oligopurine sequence used for triple helix formation is boxed. (contained within SEQ ID NOs 18 and 19). The sequence of two GOREC molecules are given. The TFOs (SEQ ID NO:10 and SEQ ID NO:11) are 5' tethered by an acridine (W) and 3' linked to a 12-nt oligonucleotide (adapter, italic letters, SEQ ID NO:9) through a tri- or hexaethyleneglycol linker (S or L, respectively). Modified nucleotides are used in TFOs: u=C5-propynyluracil; O=C5-methylcytosine; g=7-deazaguanine; t and o=thymine and C5-methylcytosine in 2'-O,4'-C bridged locked nucleic acids, respectively.

An episomal assay system based on a plasmid carrying an enhanced GFP gene (eGFP) was thus set up to validate the so-called <<GOREC>> method. A stop codon was introduced in the eGFP gene, the homologous recombination by a wild type single-stranded donor DNA (ssDNA) or double-standed donor DNA (dsDNA) around the stop codon will suppress the stop codon and therefore restore eGFP expression which can be easily monitored by GFP fluorescence. A triple helix forming sequence (TPX) was introduced at the end of eGFP gene (FIG. 7).

Materials and Methods

Oligonucleotides

Purified oligonucleotides were purchased from Eurogentec (Sering, Belgium), except TFO2-L which was bought from Proligo LLC (Boulder, U.S.A.). Concentrations were determined spectrophotometrically at 25° C. using molar extinction coefficients at 260 nm calculated from a nearest-neighbor model.

Construction of Plasmids

The pEGFP-C1 plasmid (Clontech, Palo Alto, U.S.A.) used in this work carry an enhanced GFP gene (eGFP).

The mutant pEGFPstop plasmid was constructed to introduce a stop mutation (TAC→TGA) at codon 66 (or nucleotide 810) of eGFP gene by site directed mutagenesis. Two separate fragments were PCR amplified from the pEGFP-C1 plasmid. Mutation was contained in the downstream primer of one fragment (from 541 to 822) and in the upstream primer of the other fragment (from 802 to 1390). After purification, the fragments were mixed together and were used as template to generate the mutant insert extending from position 541 to 1390. After digestion with BsrgI and Eco47III the mutant fragment was ligated into pEGFP-C1 also digested by BsrgI and Eco47III. Colonies generated from transformation into DH5α were screened by digestion with DdeI because the stop mutation introduced a new DdeI restriction site. A positive clone named pEGFPstop was sequenced to confirm mutation and subsequently used for pEGFPstopTPX construction and targeting experiments.

The pEGFP-TPX and pEGFPstopTPX plasmids contained the sequence of triple helix site (TPX) in the multiple cloning site of pEGFP-C1 vector and were constructed with synthetic oligonucleotides. Oligonucleotides 5'-ccgggtctagaaaagaaaagggggatacgcgtggccagc-3' (SEQ ID n°5) and 5'-ccggcgtggccacgcgtatcccccctttctttctagac-3' (SEQ ID n°6) were hybridized and ligated into pEGFP-C1 and pEGFPstop vectors digested with Ava I endonucleases (cutting positions 1344 and 1387). Ligation products were screened by XbaI digestion after DH5α transformation. Positive clones with TPX sequence had a new XbaI recognition site and were sequenced to confirm the presence of TPX sequence.

The pGL3 and pBSKII vectors were used as control vectors, they express the luciferase and the lacZ genes, respectively Single-Stranded Donor DNA Fragments Single-stranded donor DNA (ssDD) fragment was first produced by PCR amplification with a biotinylated primer 5'-ccggtcgccaccatggtgagc-3' (SEQ ID n°7, primer "601" in FIG. 7) and an unmodified primer 5'-cgcgtggccagctcgagatc-3' (SEQ ID n°8, primer "1360" in FIG. 7) and pEGFP-TPX as template. A 759-bp double strand amplicon was obtained and purified by gel (QIAEX II system, Qiagen). Amplicons were incubated one hour at room temperature with streptavidin magnasphere paramagnetic (Promega) in 500 μl SSC 0.5×, washed twice with SSC 0.1× and denatured with 100 μl of NaOH 0.2 M 5 minutes. The eluted non biotinylated ssDNA was then precipitated in isopropanol. Quality of ssDD was analyzed by agarose gel electrophoresis and quantity was measured by spectrophotometer.

Double-Stranded Donor DNA Fragment

Double-stranded donor DNA (dsDD) were produced by using an unmodified primer 5'-ccggtcgccaccatggtgagc-3' (SEQ ID n°7, primer "601") and the adapter segment (5'-cgcgtggccagc-3', SEQ ID n°9) of the GOREC molecule (which is a part of the primer "1360" in FIG. 7) for PCR amplification to obtain a covalently linked dsDD with TFO guides. A 759-bp double strand amplicon was obtained and purified by gel (QIAEX II system, Qiagen). Quality of dsDD was analyzed by agarose gel electrophoresis and the quantity was measured by spectrophotometer. It should be noted that such a PCR prepared dsDNA is covalently linked to TFO. It is easy to convert this covalent GOREC molecule into a non covalent one simply by introducing one or several ribonucleotides at the 3'-end of the adapter domain. The ribonucleotide can be degraded by a mild alkaline treatment or an enzymatic (for instance, RNase A) digestion after PCR amplification.

GOREC Molecules

The oligopyrimidine•oligopurine sequence used for triple helix formation is provided hereunder (also shown in FIG. 7):

TFO1-S 3'-CGACCGGTGCGC-S-GgGGgGuuuTOTuuuOu-5'-W (SEQ ID n°9-S-SEQ ID n°10-5'-W), TFO2-L 3'-CGACCGGTGCGC-L-GGGGGtTtToTtTtOt-5'-W (SEQ ID n°9-L-SEQ ID n°11-5'-W).

The TFOs are 5' tethered by an acridine (W) and 3' linked to a 12-nt oligonucleotide (adapter, italic letters) through a tri- or hexaethyleneglycol linker (S or L, respectively). Modified nucleotides are used in TFOs: u=C5-propynyluracil; O=C5-methylcytosine; g=7-deazaguanine; t and o=thymine and C5-methylcytosine in 2'-O,4'-C bridged locked nucleic acids, respectively.

The adapter sequence, a 12-nt oligonucleotide (SEQ ID n°9), is complementary of the ssDNA.

GOREC molecules were obtained either by mixing the TFO guides (covalently linked to adapter) with the ssDD by heating one minute at 100° C. and then returning to room temperature in 6 hours in order to hybridize the adapter to the 5' end of the ssDD, or using the adapter as a primer (instead of the primer 1360) for PCR amplification to obtain a covalently linked dsDD with TFO guides.

Cell Culture and Transfection

For assays 1 and 2, CHO DRA10 cells were grown in Dulbecco's modified Eagle's medium (DMEM, Gibco) supplement with inactivated fetal bovin serum, antibiotics (100 U/ml streptomycine and 100 U/ml penicillin) and 2 mM glutamine. Two protocols were used:

The first involves two steps. First, the cells CHO-DRA10 (9 millions) were electroporated at 120 volts, 2 pulses in 600 μl of Opti (Gibco) with 48 μg of plasmid DNA, peGFPstop__TPX, and deposited on a 24 well-plate. Secondly, the cells were transfected by PEI. 4 hours after the first transfection, the recombinant DNA and the GOREC molecule were co-transfected with PEI.

The second is a one step protocol, the day before transfection 70000 CHODRA10 cells were seeded in 24 wellplates. The plasmid peGFPstop__TPX was co-transfected with ssDNA with or without the GOREC molecule. Briefly, DNA and PEI were prepared as previously described.

All samples were duplicated. The ssDNA, GOREC molecules and pGL3 were preincubated and completed with pBSKII to maintain constant DNA quantity (1 μg). The PEI solution was then added to the DNA solution. This solution was incubated at room temperature for 10 minutes. The final volume of transfection (20 μl) is deposited in the 100 μl of Opti well. We have used 3.6 PEI (nitrogen)/DNA (phosphate). 2 hours after transfection with PEI, the cells were washed and 1 ml of fresh medium added. To evaluate the number of corrected cells, 48 hours after transfection, the plate was observed in a fluorometric microscope and the corrected cells were counted. In order to count total lives cells, cells were harvested from the plate with trypsine and counted. The cells were lyzed with RLB buffer and the luciferase activity was measured.

For assays 3 and 4, CHO cells were derived from CHO-K1 cells (ATCC, Rockville, U.S.A.) and were generous gifts from Dr. B. Lopez (CEA, Fontenay-aux-roses, France). Cells were grown in Dulbecco's modified Eagle's medium (Gibco BRL) supplemented with 10% fetal bovine serum, 100 U/ml streptomycin, 100 U/ml penicillin and 2 mM glutamine.

For transfection experiments, 2×10$^5$ cells were seeded per well in a 24-well plate 24 h before transfection. About 1.2 μg of DNA (plasmids, donor DNA and/or GOREC molecule) was incubated 20 minutes at room temperature with 2 μg of polyethyleneimine (PEI Exgen 500, Euromedex, Souffelweyersheim, France) in a final volume of 20 μl NaCl 0.9%. After 2 hours incubation at 37° C., the cells were washed and 1 ml of fresh medium added.

Gene Correction Efficiency

To evaluate the efficiency of gene correction, 48 hours after transfection, cells were observed by epifluorescence microscopy (DM-IL, Leica Microsystemes) and were counted by fluorescence-activated cell sorting device (FACS, Becton-Dickinson). The numbers of fluorescent cells obtained 48 hours after transfection with pEGFP-stopTPX in the presence of GOREC molecules were reported to the number of fluorecent cells obtained with pEGFP-TPX. That ratio was used as an evaluation of extrachromosomal gene correction efficiency. Assays were performed in triplicates.

Results

Gene Correction with Single-stranded Donor DNA

Figure 8:
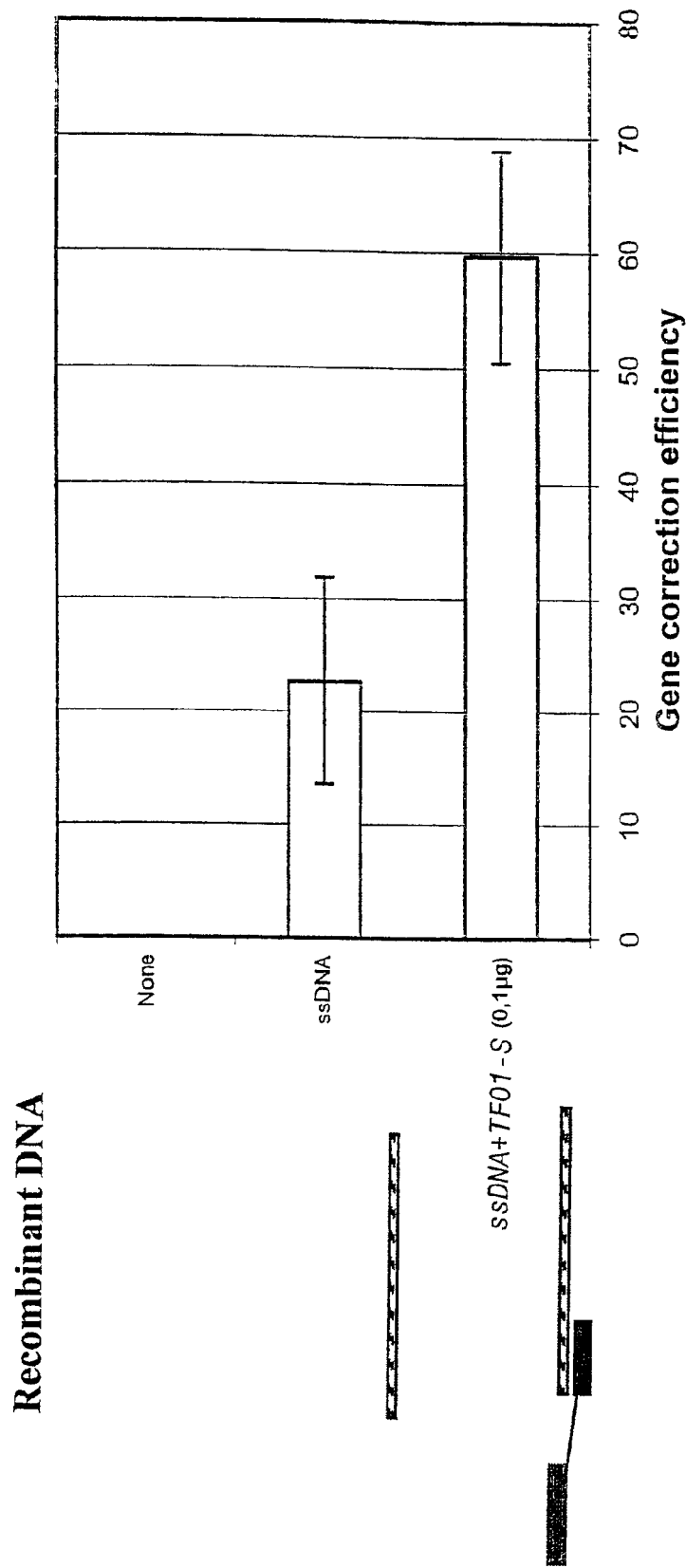
FIG. 8 represents the gene correction efficiency for ssDNA and ssDNA+oligonucleotide TFO1-S with DRA 10 cell line.

Assay 1:

The plasmid peGFPstop_TPX containing a stop codon in the eGFP gene and an oligopyrimidine•oligopurine sequence for DNA targeting by triple helix formation (TPX) was first electroporated into the CHO DRA10 cells. 4 hours later, the single-strand recombinant DNA (0.5 μg) with or without GOREC molecules, along with the plasmid pGL3 (0.03 μg) carrying a luciferase gene used for assessing the transfection yield were co-transfected by polycations (polyethyleneimine, PEI). The transfection caused cell mortality were about 40% and 10% for electroporation and for PEI transfection, respectively. The gene correction can be monitored by the restored GFP fluorescence in the transfected cells, and was measured by fluorescence microscopy. The apparent gene correction efficiency is the ratio of the number of GFP fluorescent cells/the number of total cells after taking into account of the transfection yield measured by luciferase activity (FIG. 8).

It was observed that the transfection of 0.5 μg single strand recombinant DNA (ssDNA) alone was able to effect gene correction as previously described in the literature, whereas no fluorescent cells were observed in the absence of ssDNA. As expected, the gene correction efficiency was enhanced when the ssDNA was co-transfected with 0.1 μg TFO1-S which forms stable triple helix under neutral pH and contains adapter for carrying the ssDNA.

Figure 9:
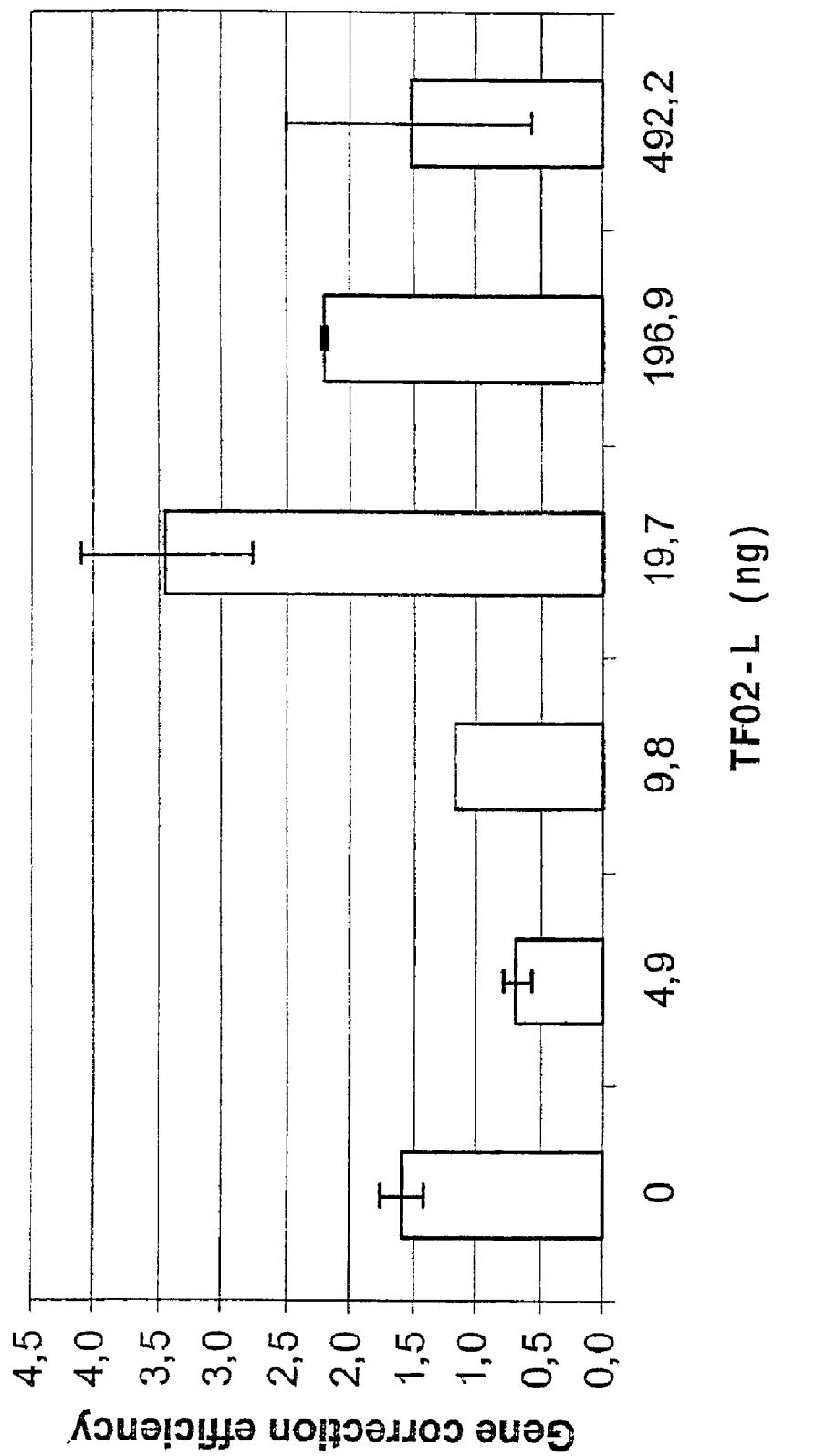
FIG. 9 represents the gene correction efficiency for ssDNA+a TFO2-L oligonucleotide with the DRA 10 cell line.

Assay 2:

In the second assay, 0.4 pg peGFPstop_TPX plasmid, 0.5μg ssDNA and the increased amount of another GOREC molecule which containing backbone modified nucleotides in the triple helix-forming domain (TFO2-L, 0–0.5 μg) was preincubated in vitro, then co-transfected into the CHO DRA10 cells with PEI. It came out that the highest apparent gene correction efficiency was achieved with 0.02 μg TFO2-L (about 1:1 ratio TFO2-L vs. ssDNA). These data indicate that the fine tunning of the amount of GOREC molecule and its ratio relative to the recombinant DNA fragment is of importance for optimizing gene correction efficiency (FIG. 9).

Figure 10:
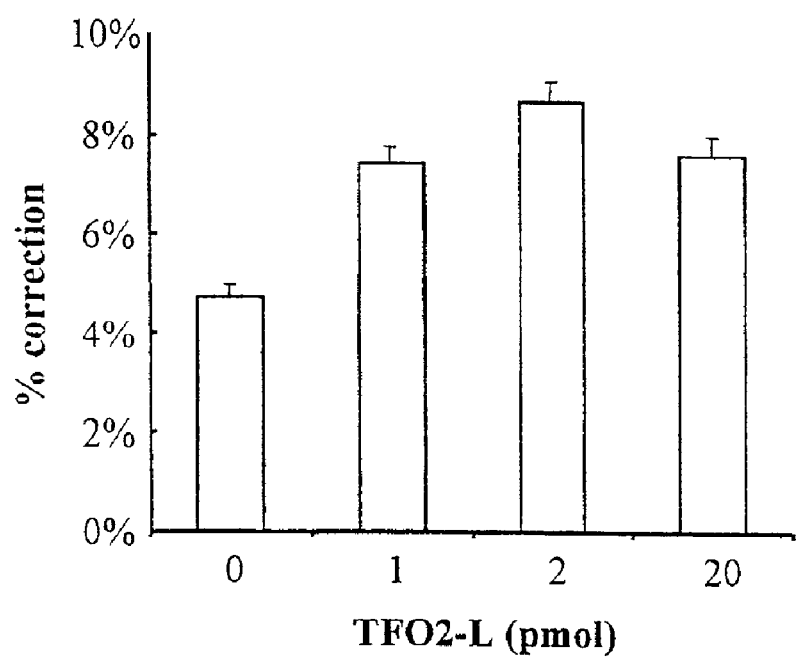
FIG. 10 displays results of the gene correction assay by single-stranded donor DNA where the amount of ssDD was kept constant (2 pmol=0.6 µg) for all points and the ssDD was titrated by increasing amount of TFO2-L (0, 1, 2, 20 pmol).

Assay 3:

In this assay, the amount of ssDD was kept constant (0.6 μg). ssDD was titrated by TFO2-L at different stoechiometry (2 to 0.1). The assays were carried out by co-transfecting 0.04 μg pEGFPstopTPX or pEGFP-TPX (as control) with either ssDD alone, or associated with the guide (TFO2-L+ssDD). After 48 hours, the number of fluorescent cells transfected by pEGFPstopTPX plasmid with various DNA fragments was counted and compared to that of the cells transfected by the control plasmid pEGFP-TPX under the same condition. The ratio of fluorescent cells was used as an evaluation of extrachromosomal gene correction efficiency. It was observed that upon 1:1 ratio (TFO2-L+ssDD), about two-fold enhancement of gene correction was obtained (FIG. 10). 10-fold excess of TFO2-L did not greatly further increase gene correction.

Assay 4: Gene Correction with Double-Stranded Donor DNA

In this assay, the adapter in TFO1-S was used as one of the primers to product a wild type eGFP fragment. Such a 759-bp double-stranded donor (dsDD) was thus covalently linked to the guide. For those skilled in the art, it is easy to convert this covalent GOREC molecule into a non covalent one simply by introducing one or several ribonucleotides at the 3'-end of the adapter segment. The ribonucleotide can be degraded by a mild alkaline treatment or an enzymatic digestion after PCR amplification.

Figure 11A:
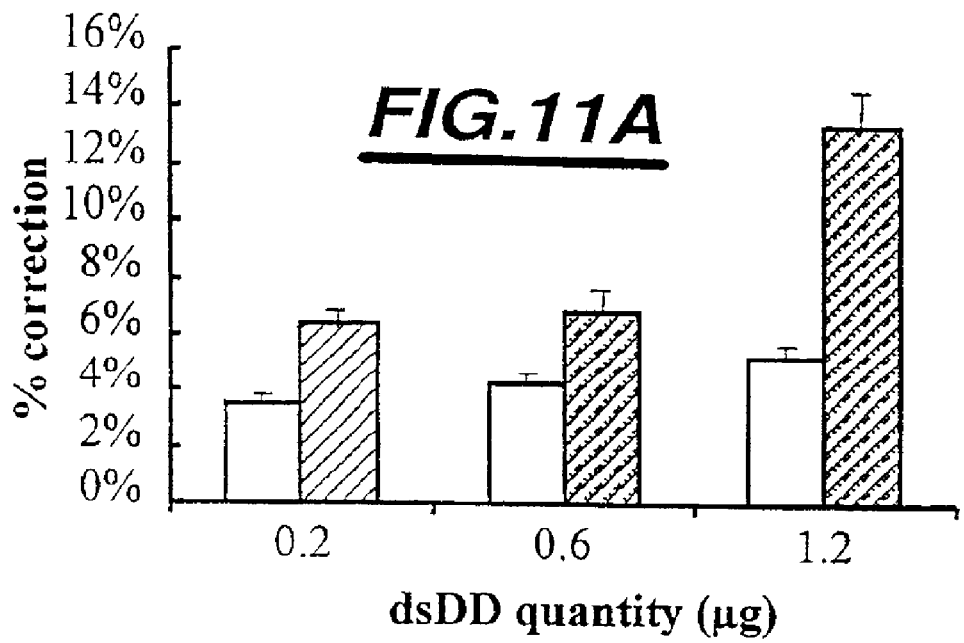
FIG. 11 shows results of the gene correction assay by double-stranded donor DNA alone (open box) or TFO1-S-dsDD (hatched box). A: The correction rate was calculated by normalizing the data obtained with pEGFPstopTPX plasmid by those with the pEGFP-TPX control plasmid. B: The ratio of the correction rates obtained for the plasmids pEGFPstopTPX and pEGFPstop.

The assays were carried out by co-transfecting 0.04 μg pEGFPstopTPX or pEGFP-TPX (as control) with either dsDD alone, or associated with the guide (TFO1-S-dsDD) in the range of 0.2–1.2 μg. They were performed in a similar way as for the ssDD assay. It was observed that the guided dsDD (TFO1-S-dsDD) was more efficient in gene correction than the unguided dsDD (FIG. 11A). The enhancement obtained by 1.2 μg TFO1-S-dsDD was about 2.6 as compared to 1.2 μg dsDD alone.

Figure 11B:
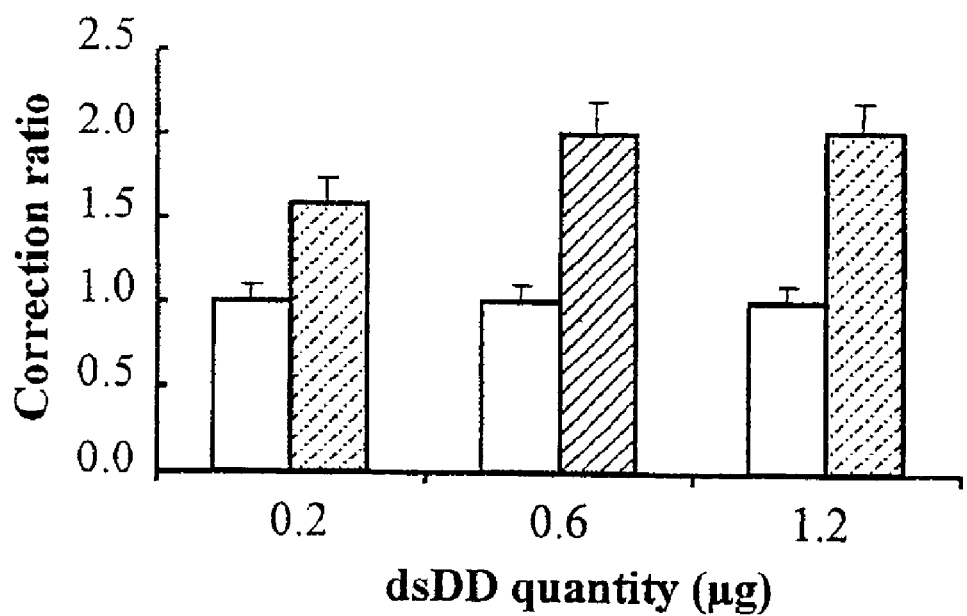

A similar assay was carried out in which the control plasmid pEGFP-TPX was replaced by the plasmid pEGFPstop, which has a stop codon but lacks the triple helix site. The ratio of the number of fluorescent cells transfected by pEGFPstopTPX and by pEGFPstop with dsDD or TFO1-S-dsDD would indicate the specificity of gene targeting by triple helix formation. As expected, the gain in gene correction by GOREC approach was evidenced by the observation that the lack of enhancement of gene correction in the cells treated by dsDD alone for all amount of transfected DNA, whereas the ratio was increased to about 1.5 and 2 for 0.2 μg and 0.6–1.2 μg transfected TFO1-S-dsDD, respectively (FIG. 11B ).

It should be noted that this simple episomal assay system does not allow quantitative assessment of the gene correction efficiency as the number of plasmid containing the target gene varies in the transfected cells and the gene correction event was counted on a all-or-none basis (fluorescent cell or not). Further experiments are required in a chromosomal assay system in order to measure unambiguously the efficiency of gene correction events.

REFERENCES

Akiyama, T. and Hogan, M. E. (1996)) *Proc. Natl. Acad. Sci. U.S.A.* 93, 12122–12127.

Alexeev, V. and Yoon, K. (1998) *Nature Biotechnol.* 16, 1343–1346.

Arimondo, P. B., Bailly, C., Boutorine, A., Sun, J. S., Garestier, T. and Hélène, C. (1999) *C. R. Acad. Sci. Paris série III*, 322, 1–6.

Asseline, U. (1999) Triple helix forming oligonucleotides. Ed. Malvy, C., Harel-Bellan, A. and Pritchard, L. L. Kluwer Academic Publisher. 63–73.

Barre, F. X., Asseline, U. and Harel-Bellan, A. (1999) *J. Mol. Biol.* 286, 1379–87

Belousov, E. S., Afonina, I. A., Kutyavin, I. V., Gall, A. A., Reed, M. W., Gamper, H. B., Wydro, R. M. and Meyer, R. B. (1998) *Nucleic Acids Res.* 26, 1324–1328.

Bollag, R. J., Waldman, A. S. and Liskay, R. M. (1989) *Ann. Rev. Genet.* 23, 199–225.

Cantor, C. R. and Warshaw, M. M. (1970) *Biopolymers* 9, 1059–1077.

Chan, P. P. and Glazer, P. M. (1997) *J. Mol. Med.* 75, 267–282.

Chan, P. P., Lin, M., Faruqi, A. F., Powell, J. seidman, M. M. and Glazer, P. M. (1999) *J. Biol. Chem.* 274, 11541–11548.

Cheng, A. J. and Vandyke, M. W. (1994) *Nucleic Acids Res.* 22, 4742–4747.

Cole-Strauss, A., Gamper, H., Holloman, W. K., Munoz, M., Cheng, N. and Kmiec, E. B. (1999) *Nucleic Acids Res.* 27, 1323–1330.

Culver, K. W., Hsieh, W. T., Huyen, Y., Chen, V., Liu, J., Khripine, Y. and Khorlin, A. (1999) *Nature Biotech.* 17, 989–993.

Escudé, C., Garestier, T. and Hélène, C. (1999) *Proc. Natl. Acad. Sci. USA* 96, 10603–10607.

Felgner et al. (1989) *Science* 337, 387–388

Frangois, J. C., Saison-Behmoaras, T., Barbier, C., Chassignol, M., Thuong, N. T. and Hélène, C. (1989) *Proc. Nati. Acad. Sci. U.S.A.* 86, 9702–9706.

Gamper, H. B., Hou, Y. M., Stamm, M. R., Podyminogin, M. A. and Meyer, R. B. (1998) *J. Am. Chem. Soc.* 120, 2182–2183.

Giovannangeli, C., Diviacco, S., Labrousse, V., Gryaznov, S., Charneau, P. and Hélène, C. (1997) *Proc. Natl. Acad. Sci. USA* 94, 79–84.

Giovannangeli, C., Perrouault, L., Escudé, C., Gryaznov, S. and Hélène, C. (1996) *J. Mol. Biol.* 261, 386–398.

Guieysse, A. L., Praseuth, D., Grigoriev, M., Harel-Bellan, A. and Hélène, C. (1996) *Nucleic Acids Res.* 24, 4210–4216.

Havre, P. A. and Glazer, P. M. (1993) *J. Virol.* 67, 7324–7331.

Havre, P. A., Gunther, E. J., Gasparro, F. P. and Glazer, P. M. (1993) *Proc. Nati. Acad. Sci. U.S.A.* 90, 7879–7883.

Hélène, C. (1991) *Anti-Cancer Drug Des.* 6, 569–584.

Kenneth W, Culver, 1999, *NatureBiotechnology*, 17, 989–993

Koshkin, K. K. & Wengel, J. *Tetrahedron*, 1998, 54, 3607–3630

Le Doan, T., Perrouault, L., Praseuth, D., Habhoub, N., Decout, J. L., Thuong, N. T., Lhomme, J. and Hélène, C. (1987). *Nucleic Acids Res.* 15, 7749–7760.

Mackey, et al., (1988) *Proc. Natl. Acad. Sci. U.S.A.* 85, 8027–8031

Maher, L. J. (1996) *Cancer Invest.* 14, 66–82.

Matteucci, M., Lin, K. Y., Huang, T., Wagner, R., Stembach, D. D., Mehrota, M. and Besterman, J. M. (1997) *J. Am. Chem. Soc.* 119, 6939–6940.

Moser, H. E. and Dervan, P. B. (1987). *Science* 238, 645–650.

Nielsen et al. (1991) *Science,* 254: 1497.

Pei, D. and Schultz, P. G. (1991) *J. Am. Chem. Soc.* 113, 9398–9400.

Povsic, T. J. and Dervan, P. B. (1990) *J. Am. Chem. Soc.* 112, 9428–9430.

Roth, D. B. and Wilson, J. H. (1986) *Mol. Cell. Biol.* 6, 4295–4304.

Sambrook, Fritsch & Maniatis (1989) *Molecular Cloning: A Laboratory Manual*, Second Edition, Cold Spring Harbor Laboratory Press, Cold Spring Harbor, N.Y.

Strobel, S. A. and Dervan, P. B. (1991) *Nature* 350, 172–174.

Sun et al. (1993) *Curr. Op Struct. Biol.* 3, 345–356

Sun, J. S., Garestier, T. and Hélène, C. (1996) *Curr. Opin. Struct. Biol.* 6, 327–333.

Takasugi, M., Guendouz, A., Chassignol, M., Decout, J. L., Lhomme, J., Thuong, N. T. and Hélène, C. (1991) *Proc. Natl. Acad. Sci. U.S.A.* 88, 5602–5606.

Thuong, N. T. and Hélène, C. (1993) *Anggew. Chem. Int. Ed.* 32, 666–690.

Wang, G., Levy, D. D., Seidman, M. M. and Glazer, P. M. (1995) *Mol. Cell. Biol.* 15, 1759–1768.

Wu et al. (1988) *J. Biol. Chem.* 263: 14621–14624.

Wu et al., (1992) *J. BioL Chem.* 267: 963–967.

Yoon, K., Cole-Strauss, A. and Kmiec, E. B. (1996) *Proc. Natl. Acad. Sci. U.S.A.* 93, 2071–2076.

All the patents and publications cited throughout the present specification are incorporated herein by reference, in their entirety.

---

What is claimed:

1. A method for effecting a homologous recombination between a double-stranded native nucleic acid segment in a cell and a donor nucleic acid segment introduced into the cell, which method comprises the steps consisting of:

a) providing a pair of primers complementary to the 5' and 3' ends of a first double-stranded native nucleic acid sequence, wherein one of the primers is a modified adapter segment which contains one or several ribonucleotide(s) at its 3'-end, wherein said adapter segment is linked to a third strand oligonucleotide which comprises a base sequence capable of forming a triple helix at a binding region on one or both strands of a second double-stranded native nucleic acid segment;

b) amplifying said first native nucleic acid sequence, c) isolating the amplification product thus obtained, d) treating the isolated amplification product in conditions sufficient to allow destruction of said ribonucleotide, thereby providing a nucleic acid targeting system comprising:

(i) said third strand oligonucleotide, (ii) said amplification product as a donor nucleic acid segment comprising a nucleic acid sequence substantially homologous to the native nucleic acid segment so that the donor sequence is capable of undergoing homologous recombination with the native sequence at the target region, (iii) said adapter segment bound to said donor nucleic acid segment through Watson-Crick base pairing, the adapter segment being linked to said third strand oligonucleotide, e) introducing said nucleic acid targeting system into a cell ex viva comprising a second native nucleic acid different from the first native nucleic acid;

f) allowing said third strand oligonucleotide to bind to the second native nucleic acid segment to form a triple helix nucleic acid, thereby inducing homologous recombination at the native nucleic acid segment target region; and g) allowing homologous recombination to occur between the native and donor nucleic acid segments;
wherein said donor nucleic acid is between more than 100 and 1,000,000 bases in length.

2. The method according to claim 1, wherein step d) comprises enzymatic or mild alkaline treatment.

* * * * *